(12) United States Patent
Fine et al.

(10) Patent No.: US 11,511,252 B2
(45) Date of Patent: *Nov. 29, 2022

(54) CONVERSION OF NITROGEN DIOXIDE (NO2) TO NITRIC OXIDE (NO)

(71) Applicant: VERO Biotech Inc., Atlanta, GA (US)

(72) Inventors: David H. Fine, Cocoa Beach, FL (US); David P. Rounbehler, Lexington, MA (US); Gregory Vasquez, Cocoa, FL (US); Bryan Johnson, Orlando, FL (US)

(73) Assignee: VERO Biotech Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/590,093

(22) Filed: Oct. 1, 2019

(65) Prior Publication Data

US 2020/0282375 A1    Sep. 10, 2020

Related U.S. Application Data

(63) Continuation of application No. 16/149,092, filed on Oct. 1, 2018, now abandoned, which is a continuation
(Continued)

(51) Int. Cl.
*B01J 12/00* (2006.01)
*A61M 16/10* (2006.01)
(Continued)

(52) U.S. Cl.
CPC ............. *B01J 12/007* (2013.01); *A61K 33/00* (2013.01); *A61M 16/10* (2013.01);
(Continued)

(58) Field of Classification Search
CPC ....... A61K 33/00; A61M 16/00; A61M 16/10; A61M 16/12; A61M 16/122;
(Continued)

(56) References Cited

U.S. PATENT DOCUMENTS 3,674,429 A   7/1972 Collins et al.
5,417,950 A   5/1995 Sheu et al.
(Continued)

FOREIGN PATENT DOCUMENTS

JP   H04316690 A   11/1992
JP   H07187622 A    7/1995
(Continued)

OTHER PUBLICATIONS

Examination Report No. 1 for Australian Application No. 2009292963, dated Dec. 18, 2015, 3 pages.
(Continued)

*Primary Examiner* — Natasha E Young

(57) ABSTRACT

A nitric oxide delivery system, which includes a gas bottle having nitrogen dioxide in air, converts nitrogen dioxide to nitric oxide and employs a surface-active material, such as silica gel, coated with an aqueous solution of antioxidant, such as ascorbic acid. A nitric oxide delivery system may be used to generate therapeutic gas including nitric oxide for use in delivering the therapeutic gas to a mammal.

8 Claims, 29 Drawing Sheets

Related U.S. Application Data of application No. 15/229,105, filed on Aug. 4, 2016, now Pat. No. 10,086,352, which is a continuation of application No. 14/270,260, filed on May 5, 2014, now Pat. No. 9,408,994, which is a continuation of application No. 13/436,018, filed on Mar. 30, 2012, now Pat. No. 8,715,577, which is a continuation of application No. 12/563,662, filed on Sep. 21, 2009, now Pat. No. 8,173,072.

(60) Provisional application No. 61/098,974, filed on Sep. 22, 2008.

(51) Int. Cl.
| | | |
|---|---|---|
| *A61M 16/12* | (2006.01) | |
| *A61K 33/00* | (2006.01) | |
| *A62B 7/08* | (2006.01) | |
| *C01B 21/24* | (2006.01) | |

(52) U.S. Cl.
CPC ............ *A61M 16/122* (2014.02); *A62B 7/08* (2013.01); *C01B 21/24* (2013.01); *A61M 2016/1025* (2013.01); *A61M 2202/0007* (2013.01); *A61M 2202/0078* (2013.01); *A61M 2202/0275* (2013.01); *A61M 2205/07* (2013.01); *A61M 2205/12* (2013.01)

(58) Field of Classification Search
CPC ...... A61M 2202/00; A61M 2202/0007; A61M 2202/0078; A61M 2202/02; A61M 2202/0266; A61M 2202/0275; A61M 2205/00; A61M 2205/07; A61M 2205/12; A61M 2016/00; A61M 2016/10; A61M 2016/1005; A61M 2016/102; A61M 2016/1025; A62B 7/00; A62B 7/08; B01J 12/00; B01J 12/007; C01B 21/00; C01B 21/20; C01B 21/24

See application file for complete search history.

(56) References Cited

U.S. PATENT DOCUMENTS

| | | |
|---|---|---|
| 5,670,125 A | 9/1997 | Sheu et al. |
| 6,187,937 B1 | 2/2001 | Fields, Jr. et al. |
| 7,947,227 B2 | 5/2011 | Fine et al. |
| 8,173,072 B2* | 5/2012 | Fine .................. C01B 21/24 |
| | | 422/129 |
| 8,211,368 B2 | 7/2012 | Fine et al. |
| 8,715,577 B2 | 5/2014 | Fine et al. |
| 9,408,994 B2 | 8/2016 | Fine et al. |
| 10,086,352 B2 | 10/2018 | Fine et al. |
| 2003/0040542 A1 | 2/2003 | Martin |
| 2006/0048779 A1* | 3/2006 | Rounbehler ........ A61M 16/104 |
| | | 128/203.12 |
| 2006/0180147 A1 | 8/2006 | Rounbehler et al. |
| 2007/0089739 A1 | 4/2007 | Fine et al. |
| 2019/0209993 A1 | 7/2019 | Fine et al. |

FOREIGN PATENT DOCUMENTS

| | | |
|---|---|---|
| JP | H1066723 A | 3/1998 |
| JP | 2007169108 A | 7/2007 |
| WO | WO-9507610 A1 | 3/1995 |
| WO | WO-9936395 A2 | 7/1999 |
| WO | WO-0108684 A1 | 2/2001 |
| WO | WO-2006023616 A2 | 3/2006 |
| WO | WO-2008076136 A1 | 6/2008 |
| WO | WO-2008118360 A1 | 10/2008 |
| WO | WO-2010033916 A1 | 3/2010 |

OTHER PUBLICATIONS

Examination Report No. 1 for Australian Application No. 2009292963, dated Nov. 7, 2014, 3 pages.
Extended European Search Report for European Application No. 09815334.9, dated Aug. 14, 2013, 6 pages.
International Search Report and Written Opinion for International Application No. PCT/US2009/057687, dated Nov. 13, 2009, 5 pages.
Notice of Reasons for Refusal for Japanese Application No. 2011-528036, dated Aug. 13, 2013, 8 pages.
Notice of Reasons for Refusal for Japanese Application No. 2014-178701, dated Oct. 20, 2015, 11 pages.
Office Action for European Application No. 09815334.9, dated Aug. 9, 2017, 5 pages.
Office Action for European Application No. 09815334.9, dated Jan. 30, 2019, 4 pages.
Office Action for European Application No. 09815334.9, dated Mar. 30, 2016, 5 pages.
Office Action for European Application No. 09815334.9, dated May 14, 2018, 5 pages.

* cited by examiner

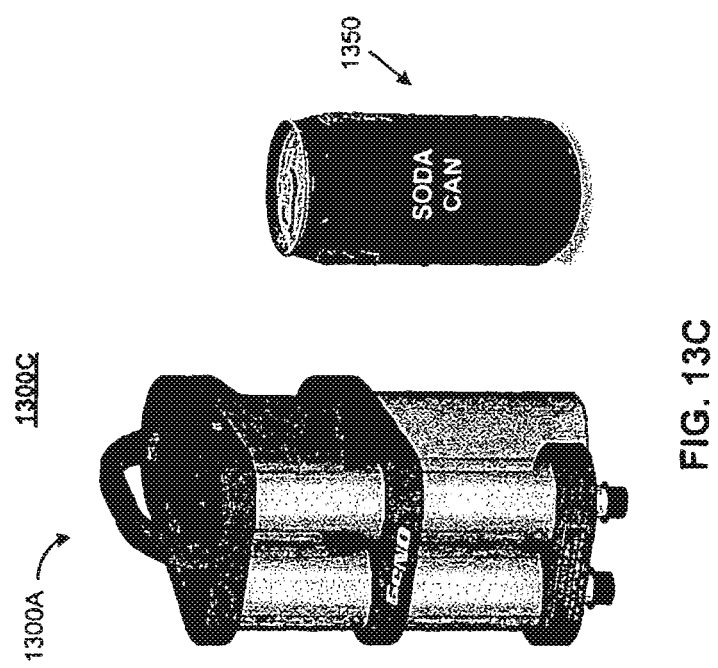

CONVERSION OF NITROGEN DIOXIDE (NO2) TO NITRIC OXIDE (NO)

CLAIM OF PRIORITY

This application is a continuation of U.S. application Ser. No. 16/149,092, filed Oct. 1, 2018, which is a continuation of U.S. application Ser. No. 15/229,105, filed Aug. 4, 2016, now U.S. Pat. No. 10,086,352, which is a continuation of U.S. application Ser. No. 14/270,260, filed May 5, 2014, now U.S. Pat. No. 9,408,994, which is a continuation of U.S. application Ser. No. 13/436,018, filed Mar. 30, 2012, now U.S. Pat. No. 8,715,577, which is a continuation of U.S. application Ser. No. 12/563,662, filed Sep. 21, 2009, now U.S. Pat. No. 8,173,072, which claims the benefit of U.S. Provisional Application No. 61/098,974, filed on Sep. 22, 2008, each of which is incorporated by reference in its entirety.

TECHNICAL FIELD

This description relates to controlled generation of nitric oxide.

BACKGROUND

Nitric oxide (NO), also known as nitrosyl radical, is a free radical that is an important signaling molecule in pulmonary vessels. Nitric oxide (NO) can moderate pulmonary hypertension caused by elevation of the pulmonary arterial pressure. Inhaling low concentrations of nitric oxide (NO), for example, in the range of 20-100 ppm can rapidly and safely decrease pulmonary hypertension in a mammal by vasodilation of pulmonary vessels.

Some disorders or physiological conditions can be mediated by inhalation of nitric oxide (NO). The use of low concentrations of inhaled nitric oxide (NO) can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide (NO) can also be used to treat chronic pulmonary hypertension, bronchopulmonary dysplasia, chronic pulmonary thromboembolism and idiopathic or primary pulmonary hypertension or chronic hypoxia. Typically, the NO gas is supplied in a bottled gaseous form diluted in nitrogen gas ($N_2$). Great care has to be taken to prevent the presence of even trace amounts of oxygen ($O_2$) in the tank of NO gas because the NO, in the presence of $O_2$, is oxidized to nitrogen dioxide ($NO_2$). Unlike NO, the part per million levels of $NO_2$ gas is highly toxic if inhaled and can form nitric and nitrous acid in the lungs.

SUMMARY

In one aspect, a system for generating a therapeutic gas including nitric oxide for use in delivering the therapeutic gas to a mammal includes a pressure regulator configured to be connected to a gas bottle having nitrogen dioxide and capable of providing diffusing gaseous nitrogen dioxide into an air flow wherein the air flow is configured to be between 5 to 60 liters per minute and a receptacle configured to attach to the pressure regulator. The receptacle includes an inlet, an outlet, and a surface-active material coated with an aqueous solution of an antioxidant. The inlet is configured to receive the air flow and fluidly communicate the flow to the outlet through the surface-active material to convert the gaseous nitrogen dioxide to nitric oxide at ambient temperature.

The air flow can be at 5 liters per minute. The receptacle can have a pressure drop of between 0.001 and 0.01 psi. Alternatively, the air flow can be at 60 liters per minute or lower. The receptacle can have a pressure drop of between 0.001 and 0.05 psi. The receptacle can include a cartridge. The surface-active material can be saturated with the aqueous solution of the antioxidant. The surface-active material can include a substrate that retains water. The surface-active material can include a silica gel. The antioxidant can include ascorbic acid. The antioxidant can include alpha tocopherol or gamma tocopherol.

The details of one or more embodiments of the invention are set forth in the accompanying drawings and the description below. Other features, objects, and advantages of the invention will be apparent from the description and drawings, and from the claims.

DETAILED DESCRIPTION

When delivering nitric oxide (NO) for therapeutic use to a mammal, it can be important to avoid delivery of nitrogen dioxide ($NO_2$) to the mammal. Nitrogen dioxide ($NO_2$) can be formed by the oxidation of nitric oxide (NO) with oxygen ($O_2$). The rate of formation of nitrogen dioxide ($NO_2$) is proportional to the oxygen ($O_2$) concentration multiplied by the square of the nitric oxide (NO) concentration—that is, $(O_2)*(NO)*(NO)=NO_2$.

A NO delivery system that converts nitrogen dioxide ($NO_2$) to nitric oxide (NO) is provided. The system employs a surface-active material coated with an aqueous solution of antioxidant as a simple and effective mechanism for making the conversion. More particularly, $NO_2$ can be converted to NO by passing the dilute gaseous $NO_2$ over a surface-active material coated with an aqueous solution of antioxidant. When the aqueous antioxidant is ascorbic acid (that is, vitamin C), the reaction is quantitative at ambient temperatures. The techniques employed by the system should be contrasted for other techniques for converting $NO_2$ to NO. Two such techniques are to heat a gas flow containing $NO_2$ to over 650 degrees Celsius over stainless steel, or 450 degrees Celsius over Molybdenum. Both of these two techniques are used in air pollution instruments that convert $NO_2$ in air to NO, and then measure the NO concentration by chemiluminescence. Another method that has been described is to use silver as a catalyst at temperatures of 160 degrees Celsius to over 300 degrees Celsius.

One example of a surface-active material is silica gel. Another example of a surface-active material that could be used is cotton. The surface-active material may be or may include a substrate capable of retaining water. Another type of surface-active material that has a large surface area that is capable of absorbing moisture also may be used.

Figure 1:
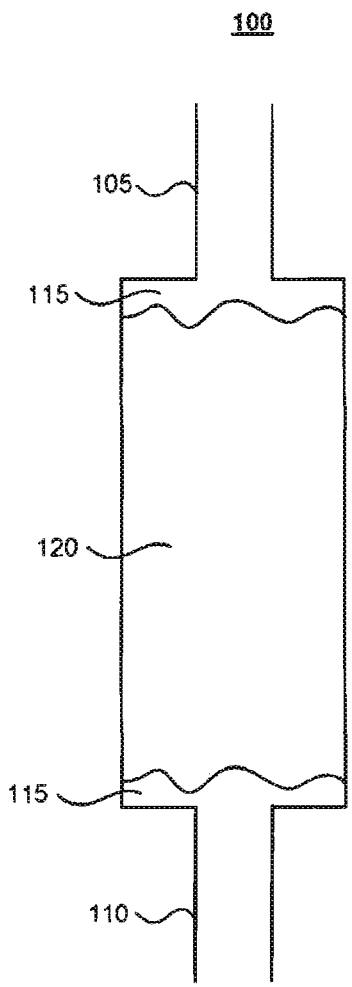
FIG. 1 is a block diagram of a cartridge that converts $NO_2$ to NO.

FIG. 1 illustrates a cartridge 100 for generating NO by converting $NO_2$ to NO. The cartridge 100, which may be referred to as a NO generation cartridge, a GENO cartridge, or a GENO cylinder, includes an inlet 105 and an outlet 110. Screen and glass wool 115 are located at both the inlet 105 and the outlet 110, and the remainder of the cartridge 100 is filled with a surface-active material 120 that is soaked with a saturated solution of antioxidant in water to coat the surface-active material. The screen and glass wool 115 also is soaked with the saturated solution of antioxidant in water before being inserted into the cartridge 100. In the example of FIG. 1, the antioxidant is ascorbic acid.

In a general process for converting $NO_2$ to NO, an air flow having $NO_2$ is received through the inlet 105 and the air flow is fluidly communicated to the outlet 110 through the surface-active material 120 coated with the aqueous antioxidant. As long as the surface-active material remains moist and the antioxidant has not been used up in the conversion, the general process is effective at converting $NO_2$ to NO at ambient temperature.

Figure 2:
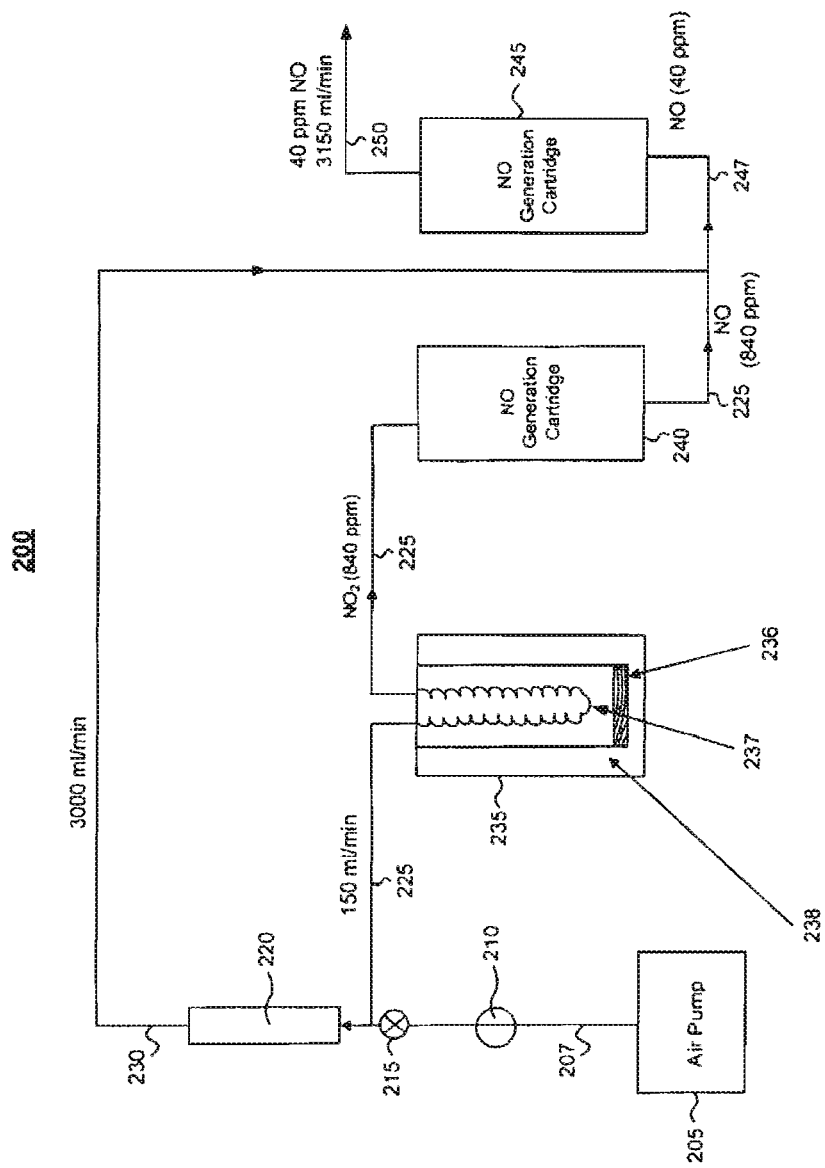
FIGS. 2-10 are block diagrams of NO delivery systems using the cartridge of FIG. 1.

The inlet 105 may receive the air flow having $NO_2$ from an air pump that fluidly communicates an air flow over a permeation tube containing liquid $NO_2$, such as in the system 200 of FIG. 2. The inlet 105 also may receive the air flow having $NO_2$, for example, from a pressurized bottle of $NO_2$, which also may be referred to as a tank of $NO_2$. The inlet 105 also may receive an air flow with $NO_2$ in nitrogen ($N_2$), air, or oxygen ($O_2$). The conversion occurs over a wide concentration range. Experiments have been carried out at concentrations in air of from about 2 ppm $NO_2$ to 100 ppm $NO_2$, and even to over 1000 ppm $NO_2$. In one example, a cartridge that was approximately 6 inches long and had a diameter of 1.5-inches was packed with silica gel that had first been soaked in a saturated aqueous solution of ascorbic acid. The moist silica gel was prepared using ascorbic acid (i.e., vitamin C) designated as A.C.S reagent grade 99.1% pure from Aldrich Chemical Company and silica gel from Fischer Scientific International, Inc., designated as S8 32-1, 40 of Grade of 35 to 70 sized mesh. Other sizes of silica gel also are effective. For example, silica gel having an eighth-inch diameter also would work.

The silica gel was moistened with a saturated solution of ascorbic acid that had been prepared by mixing 35% by weight ascorbic acid in water, stirring, and straining the water/ascorbic acid mixture through the silica gel, followed by draining. It has been found that the conversion of $NO_2$ to NO proceeds well when the silica gel coated with ascorbic acid is moist. The conversion of $NO_2$ to NO does not proceed well in an aqueous solution of ascorbic acid alone.

The cartridge filled with the wet silica gel/ascorbic acid was able to convert 1000 ppm of $NO_2$ in air to NO at a flow rate of 150 ml per minute, quantitatively, non-stop for over 12 days. A wide variety of flow rates and $NO_2$ concentrations have been successfully tested, ranging from only a few ml per minute to flow rates of up to 5,000 ml per minute. The reaction also proceeds using other common antioxidants, such as variants of vitamin E (e.g., alpha tocopherol and gamma tocopherol).

The antioxidant/surface-active material GENO cartridge may be used for inhalation therapy. In one such example, the GENO cartridge may be used as a $NO_2$ scrubber for NO inhalation therapy that delivers NO from a pressurized bottle source. The GENO cartridge may be used to remove any $NO_2$ that chemically forms during inhalation therapy. This GENO cartridge may be used to help ensure that no harmful levels of $NO_2$ are inadvertently inhaled by the patient.

First, the GENO cartridge may be used to supplement or replace some or all of the safety devices used during inhalation therapy in conventional NO inhalation therapy. For example, one type of safety device warns of the presence of $NO_2$ in air when the concentration of $NO_2$ exceeds a preset or predetermined limit, usually 1 part per million or greater of $NO_2$. Such a safety device may be unnecessary when a GENO cartridge is positioned in a NO delivery system just prior to the patient breathing the NO laden air. The GENO cartridge converts any $NO_2$ to NO just prior to the patient breathing the NO laden air, making a device to warn of the presence of $NO_2$ in air unnecessary.

Furthermore, a GENO cartridge placed near the exit of inhalation equipment and gas plumbing lines (which also may be referred to as tubing) also reduces or eliminates problems associated with formation of $NO_2$ that occur due to transit times in the ventilation equipment. As such, use of the GENO cartridge reduces or eliminates the need to ensure the rapid transit of the gas through the gas plumbing lines that is needed in conventional applications. Also, a GENO cartridge allows the NO gas to be used with gas balloons to control the total gas flow to the patient.

Alternatively or additionally, a $NO_2$ removal cartridge can be inserted just before the attachment of the delivery system to the patient to further enhance safety and help ensure that all traces of the toxic $NO_2$ have been removed. The $NO_2$ removal cartridge may be a GENO cartridge used to remove any trace amounts of $NO_2$. Alternatively, the $NO_2$ removal cartridge may include heat-activated alumina. A cartridge with heat-activated alumina, such as supplied by Fisher Scientific International, Inc., designated as A505-212, of 8-14 sized mesh is effective at removing low levels of $NO_2$ from an air or oxygen stream, and yet lets NO gas pass through without loss. Activated alumina, and other high surface area materials like it, can be used to scrub $NO_2$ from a NO inhalation line.

In another example, the GENO cartridge may be used to generate NO for therapeutic gas delivery. Because of the effectiveness of the NO generation cartridge in converting toxic $NO_2$ to NO at ambient temperatures, liquid $NO_2$ can be used as the source of the NO. When liquid $NO_2$ is used as a source for generation of NO, there is no need for a pressurized gas bottle to provide NO gas to the delivery system. An example of such a delivery system is described in more detail with respect to FIG. 2. By eliminating the need for a pressurized gas bottle to provide NO, the delivery system may be simplified as compared with a conventional apparatus that is used to deliver NO gas to a patient from a pressurized gas bottle of NO gas. A NO delivery system that does not use pressurized gas bottles may be more portable than conventional systems that rely on pressurized gas bottles.

FIGS. 2-14 illustrate techniques using silica gel as the surface-active material employed in a GENO cartridge. As discussed previously, silica gel is only one example of a surface-active material that may be used in a NO generation system or cartridge.

FIG. 2 illustrates a NO generation system 200 that converts liquid $NO_2$ to NO gas, which then may be delivered to a patient for NO inhalation therapy. In general, a flow of air generated by an air pump 205 is passed through a gas permeation cell 235 having liquid $NO_2$ and its dimer $N_2O_4$ (collectively, 236). The air flow exiting the gas permeation cell 235 includes gaseous $NO_2$, which is converted to NO gas by a NO generation cartridge 240. The NO gas mixture may be delivered to a patient for inhalation therapy, for example, using a mask, a cannula, or a ventilator. The concentration of NO in the NO gas mixture delivered to the patient may be controlled by controlling the temperature of the gas permeation cell 235 or the air flow rate through the flow meter 220.

More particularly, the system 200 includes an air pump 205, a regulator 210, a flow diverter 215 and a flow meter 220. The system is configured such that air flow 207 from the air pump 205 is divided into a first flow 225 of 150 ml/min and a second flow 230 of 3000 ml/min. The air flow 207 may be dry or moist.

The flow 225 is passed through a gas permeation cell 235 containing liquid $NO_2$ and its dimer $N_2O_4$ (collectively, 236) and a gas permeation tube 237. The permeation cell 235 also may be referred to as a permeation generator, a permeation device or a permeation tube holder. The $NO_2$ diffuses through the gas porous membrane of the gas permeation cell 235 into the flow 225. In one example, the flow 225 of 150 ml/min of air is allowed to flow through the permeation tube 237, such as a permeation tube supplied by KinTek Corporation of Austin, Tex. The permeation tube 237 is designed to release $NO_2$ at a steady rate such that the gas stream leaving the permeation tube in the flow 225 contains about 840 ppm of $NO_2$ when the permeation tube 237 is at a temperature of 40 degrees Celsius. The region 238 is temperature controlled to maintain a temperature of approximately 40 degrees Celsius. As discussed more fully below, maintaining the temperature of the permeation cell 235 helps to control the concentration of NO delivered to the patient.

The 150 ml of air containing 840 ppm of $NO_2$ then flows through a NO generation cartridge 240. In this example, the NO generation cartridge 240 is 6 inches long with a diameter of 1.5 inches and contains moist ascorbic acid on silica gel, which serves as the conversion reagent. The NO generation cartridge 240 may be an implementation of cartridge 100 of FIG. 1. The air stream 225 exiting from the NO generation cartridge 240 contains 840 ppm of NO, with all or essentially all of the $NO_2$ having been converted to NO.

The 225 flow of 150 ml/min with 840 ppm NO then mixes with the flow 230 of 3000 ml/min of air or oxygen to produce a flow 247 of 3150 ml/min containing 40 ppm of NO. After mixing, the flow 247 passes through a second NO generation cartridge 245 to remove any $NO_2$ that may have been formed during the dilution of NO when the flows 225 and 230 were mixed. The NO generation cartridges 240 and 245 may be sized the same, though this need not necessarily be so. For example, the NO generation cartridge 245 may be sized to have a smaller $NO_2$ conversion capacity than the NO generation cartridge 240. The resulting flow 250 of air having NO is then ready for delivery to the patient. The system 200 may be designed to produce a steady flow of NO gas for a period as short as a few hours or as long as 14 days or more. In one test, the system 200 was shown to deliver a steady flow of 40 ppm NO gas in air, without $NO_2$, for over 12 days, where the NO and $NO_2$ concentrations were measured by a chemiluminescent gas analyzer.

As an alternative to the system 200, a NO generation system may include a permeation tube that has a larger flow capacity than the permeation tube 237. In such a case, the larger permeation tube may be able to process all of the inhaled air needed to be delivered to the patient so that, for example, the flow 230 and the conversion tube 245 are not necessary.

The system 200 can be made portable, for example, if the air pump 205 used to supply the air is a portable air pump, such as a simple oil free pump. If oxygen-enriched air is needed by the patient, oxygen can be supplied in addition to, or in lieu of, the air supplied by the air pump 205. Oxygen can be supplied, for example, from an oxygen tank or a commercially available oxygen generator. Oxygen also can be supplied from a tank that has $NO_2$ mixed with $O_2$.

In some implementations, the permeation cell 238 and/or the two conversion cartridges 240 and 245 may be disposable items.

The concentration of NO in the flow 250 exiting the system 200 is independent of the flow 225 through the permeation cell 235, as long as the flow 225 is greater than a few milliliters per minute. The concentration of NO in the flow 250 is a function of the temperature of the permeation cell 235 and to a lesser degree the air flow rate 230. For example, with a constant air flow rate 230, the system 200 is designed to deliver 40 ppm NO at a temperature of 40 degrees Celsius; however, the concentration of NO can be reduced to 20 ppm NO at 30 degrees Celsius and increased to 80 ppm NO at 50 degrees Celsius. As such, a temperature controller can be used to adjust the concentration of the NO gas to be delivered. Once the desired NO concentration is selected and the temperature controller is set to maintain the particular temperature to deliver the desired concentration, the delivery rate of NO gas at the desired concentration remains constant. One example of a temperature controller is an oven, such as an oven available from KinTek Corporation, in which the permeation tube is placed. Another example of a temperature controller is a beaker of de-ionized water placed on a hot plate where the permeation tube is placed in the beaker. A thermometer may also be placed in the beaker to monitor the temperature of the water.

The NO generation system can be used to deliver a steady flow of NO gas mixture for use with a cannula, with the excess gas being vented to the environment. The NO generation system can be used with a ventilator, and, in such a case, the delivery from the NO generator must remain steady and cannot be shut off without endangering the patient receiving the NO. To handle the increased flow necessary during the air intake to the patient, the NO gas mixture may be used to inflate and then deflate a flexible bag. If the air flow to the patient is delayed in any way, a NO generation cartridge can be inserted in the NO generation system at the point immediately prior to inhalation to remove any $NO_2$ that may form from NO reacting with $O_2$ during such a delay. This helps to ensure that even very small amounts of $NO_2$ that may be formed in the bag during the delay are removed prior to the therapeutic gas flow being inhaled by the patient.

A detector can be included in the therapeutic gas delivery system 200 to detect the concentration of NO in the therapeutic gas stream. The detector can also detect the concentration of $NO_2$ in the therapeutic gas, if necessary, and may provide a warning if the NO concentration is outside a predetermined range or if the concentration of $NO_2$ is above a threshold value. Examples of monitoring techniques include chemiluminescence and electrochemical techniques. The presence of nitric oxide can be detected by, for example, a chemiluminescence detector.

Figure 3:
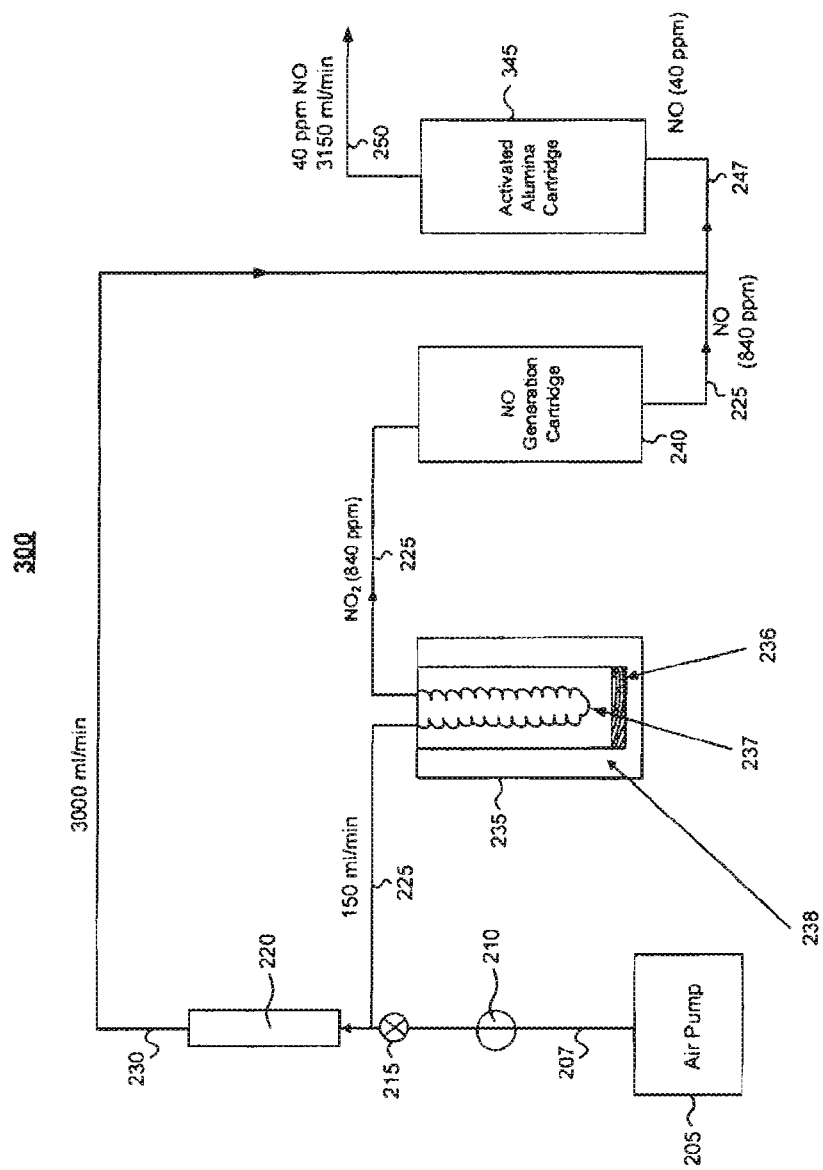

FIG. 3 depicts a NO generation system 300 that converts liquid $NO_2$ to NO gas, which then may be delivered to a patient for NO inhalation therapy. In contrast to the NO generation system 200 of FIG. 2, the NO generation system 300 includes an activated alumina cartridge 345. The activated alumina cartridge 345 removes any $NO_2$ that forms during a delay. In contrast to the NO generation cartridge 240, which removes the $NO_2$ by converting the $NO_2$ to NO, and thereby quantitatively recovering the $NO_2$, the activated alumina cartridge 345 removes $NO_2$ from the process gas stream without generating NO.

Figure 4:
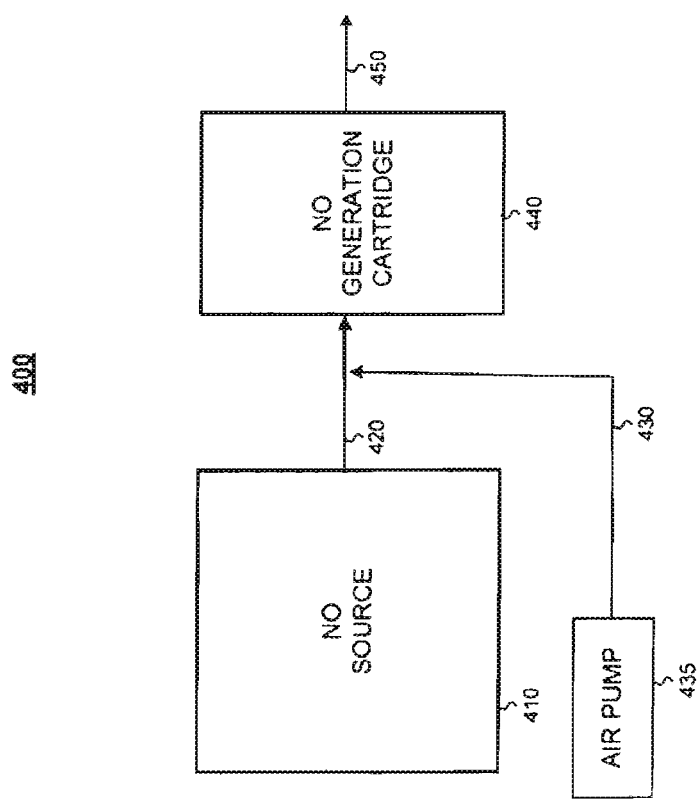

FIG. 4 illustrates a therapeutic gas delivery system 400 that uses a NO generation cartridge 440, which may be an implementation of NO generation cartridge 100 of FIG. 1. The system 400 uses a NO source 410 to provide gaseous NO in a flow 420 through tubing. In one example, the NO source 410 may be a pressurized bottle of NO. A flow of air 430 through the tubing is generated by an air pump 435 and is mixed with the flow 420. The air flow entering the NO generation cartridge 440 includes gaseous NO. Any $NO_2$ gas that may have formed in flow 420 is removed by the NO generation cartridge 440. The air flow 450 exiting the NO generation cartridge 440 includes therapeutic NO gas but is devoid of toxic levels of $NO_2$. The air flow 450 then may be delivered to a patient for NO inhalation therapy.

Figure 5:
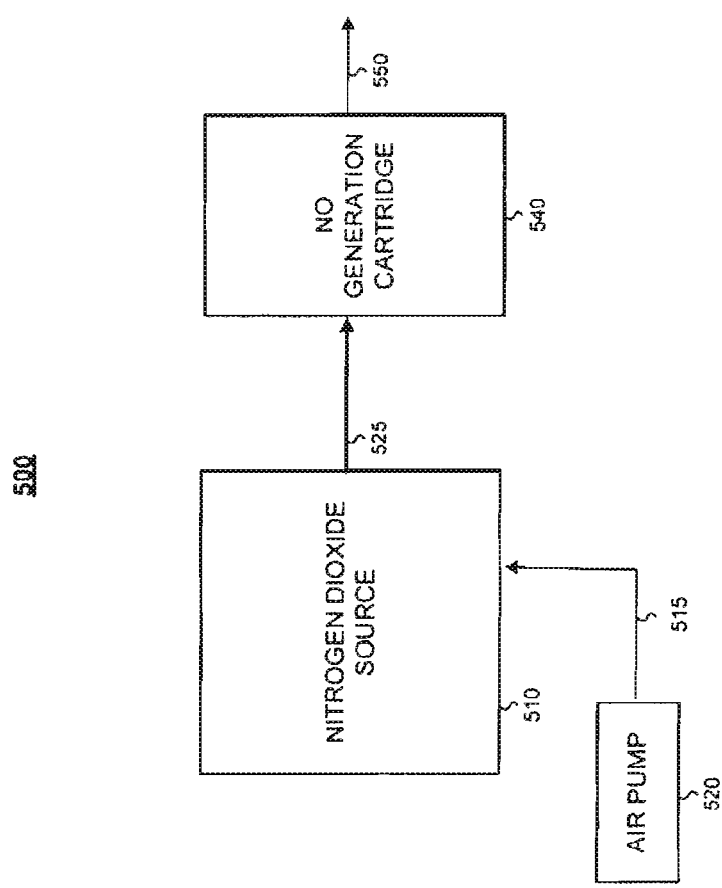

FIG. 5 illustrates a therapeutic gas delivery system 500 that uses a NO generation cartridge 540, which may be an implementation of NO generation cartridge 100 of FIG. 1. In contrast to therapeutic gas delivery system 400 of FIG. 4, the system 500 generates NO from a $NO_2$ source 510. The $NO_2$ source 510 may use diffuse liquid $NO_2$ in an air flow 515 generated by an air pump 520 such that the flow 525 exiting the $NO_2$ source 510 includes gaseous $NO_2$. In some implementations, $NO_2$ source 510 may be a pressurized bottle of $NO_2$.

In any case, the air flow 525 entering the NO generation cartridge 440 includes gaseous $NO_2$. The NO generation cartridge 440 converts the $NO_2$ gas in flow 525 to NO. The air flow 550 exiting the NO generation cartridge 540 includes therapeutic NO gas but is devoid or essentially devoid of $NO_2$. The air flow 550 then may be delivered to a patient for NO inhalation therapy.

Figure 6:
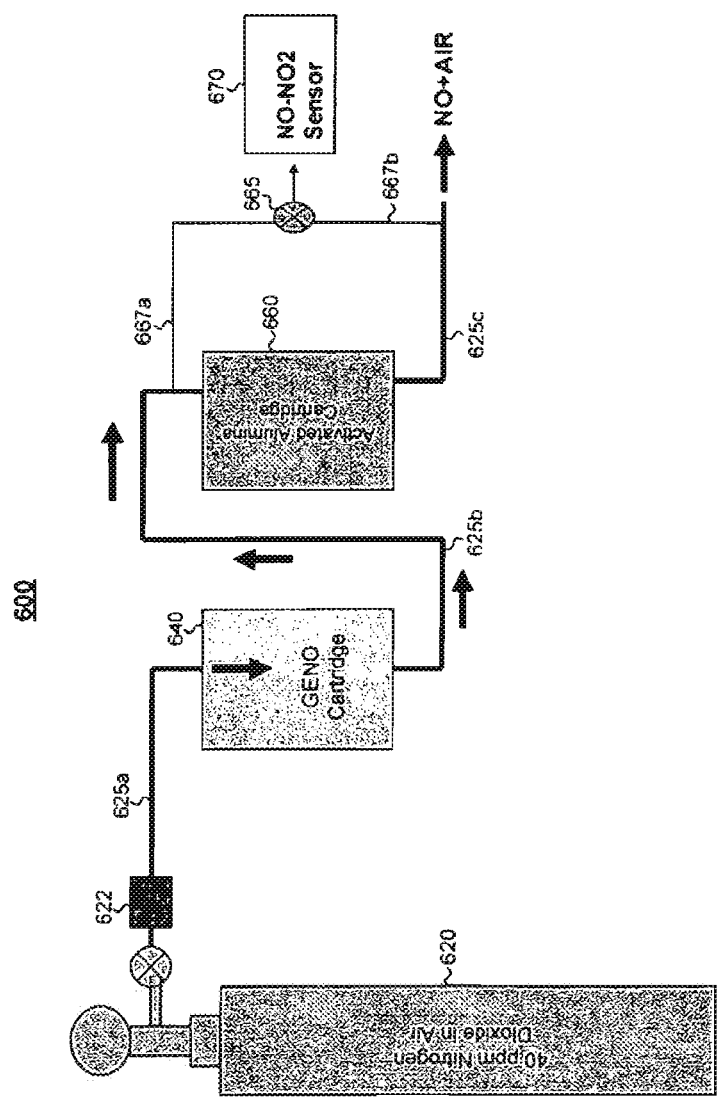

FIG. 6 illustrates a GENO pressure tank system 600 for delivering therapeutic gas. The system 600 includes a tank 620 having 40 ppm $NO_2$ in air, which is commercially available, and a flow controller 622. In one example of tank 620, a 300 cu. ft. tank lasts 1.2 days at an air flow of 5 L/min.

An air flow 625a of $NO_2$ in air exits the flow controller 622 and enters a GENO cartridge 640. The GENO cartridge 640 uses the $NO_2$ as a precursor and converts the $NO_2$ to NO. The air flow 625b exiting the GENO cartridge 640 includes therapeutic NO gas. The air flow 625b enters an activated alumina cartridge 660 to remove any $NO_2$ in the air flow 625b. The air flow 625c that exits the activated alumina cartridge 660 is delivered to a patient for NO inhalation therapy.

The system 600 includes a NOx sample valve 665 and a NO—$NO_2$ sensor 670 operable to detect $NO_2$. A NO—$NO_2$ sensor also may be referred to as a NO—$NO_2$ detector. The NOx sample valve 665 is operable to provide air samples from air flows 667a and 667b to the NO—$NO_2$ sensor 670. Using the NO—$NO_2$ detector 670 to detect the presence of any $NO_2$ in air flow 667a may provide an indication of a failure of the GENO cartridge 640, and, as such, provides a prudent safeguard to ensure that no toxic $NO_2$ is delivered to the patient.

In some implementations, the activated alumina cartridge 660 may be replaced with a GENO cartridge.

In some implementations, the GENO cartridge is attached to the output of a pressurized gas bottle that has special threads such that the output from the gas bottle can only be interfaced to a GENO cartridge. For example, the gas bottle may be filled with breathable oxygen gas containing $NO_2$ at a concentration of about 10 to 100 ppm. Such a system may use the pressure of the gas bottle to drive the therapeutic gas to the patient and may have no moving parts, electronics or pumps. Alternatively, the gas bottle may be filled with air that includes $NO_2$. The use of air or oxygen gas in the pressurized gas bottle may offer advantages over a conventional method of providing NO in inert nitrogen gas, which also necessitated the mixing and instrumentation needed to safely dilute the concentrated NO gas to a therapeutic dose.

Figure 7:
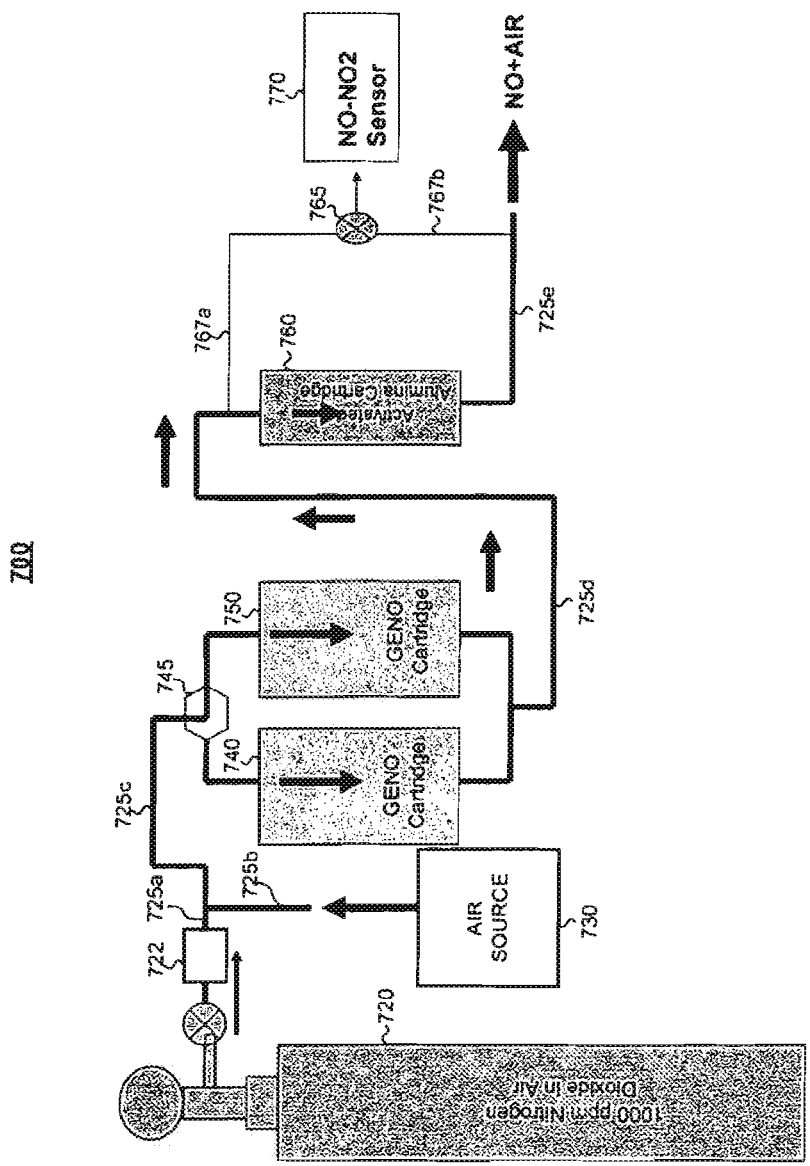

FIG. 7 illustrates a GENO high-concentration $NO_2$ pressure system 700 for delivering therapeutic gas. In contrast to the system 600 of FIG. 6, the system 700 includes two GENO cartridges 740 and 750 and a switching valve 745 to control which of the GENO cartridges 740 or 750 is used. When a NO—$NO_2$ detector 770 detects the presence of $NO_2$ in the air flow 725d exiting the GENO cartridge being used, the switching valve 745 can be manipulated to switch the air flow 725c to pass through the other GENO cartridge 740 or 750. The ability to switch to a second GENO cartridge in the event of failure of a first GENO cartridge provides an additional layer of safety for the patient to whom the therapeutic gas is being delivered.

More particularly, the system 700 includes a tank 720 having 1000 ppm $NO_2$ in air and a flow controller 722. In the example, the tank 720 is a 150 cu. ft. tank at 2250 psi and provides an air flow of 125 cc/min. At an air flow of 5 L/min of 40 ppm delivered to the patient, the tank 720 lasts approximately 23 days. The tank 720 is able to provide an air flow for a longer period than the expected life of each GENO cartridge 740 and 750, which is, in the cartridge used in this example, less than two weeks. As such, the ability to switch from one GENO cartridge to another GENO cartridge helps to ensure that the contents of the tank are used or substantially used.

An air flow 725a of $NO_2$ in air exits the flow controller 722 and is mixed with an air flow 725b of 5 L/min that is generated by an air source 730, such as an air pump. The resulting air flow 725c enters the switching valve 745. The switching valve 745 controls which of the GENO cartridges 740 or 750 receives the air flow 725c. As shown, the switching valve 745 is set such that the air flow 725c is provided to the GENO cartridge 750. The GENO cartridge 750 converts the $NO_2$ in the air flow 725c to NO. The air flow 725d exiting the GENO cartridge 725d includes therapeutic NO gas. The air flow 725d enters an activated alumina cartridge 760 to remove any $NO_2$ in the air flow 725d. The air flow 725e that exits the activated alumina cartridge 760 is delivered to a patient for NO inhalation therapy.

The system 700 includes a $NO_x$ sample valve 765 and an NO—$NO_2$ sensor 770 operable to detect $NO_2$. The $NO_x$ sample valve 765 is operable to provide air samples from air flows 767a and 767b to the NO—$NO_2$ sensor 770. Using the NO—$NO_2$ sensor 770 to detect the presence of any $NO_2$ in air flow 767a may provide an indication of a failure of the GENO cartridge being used so that the second GENO cartridge may be used. In some implementations, the activated alumina cartridge 760 may be replaced with a GENO cartridge.

Figure 8:
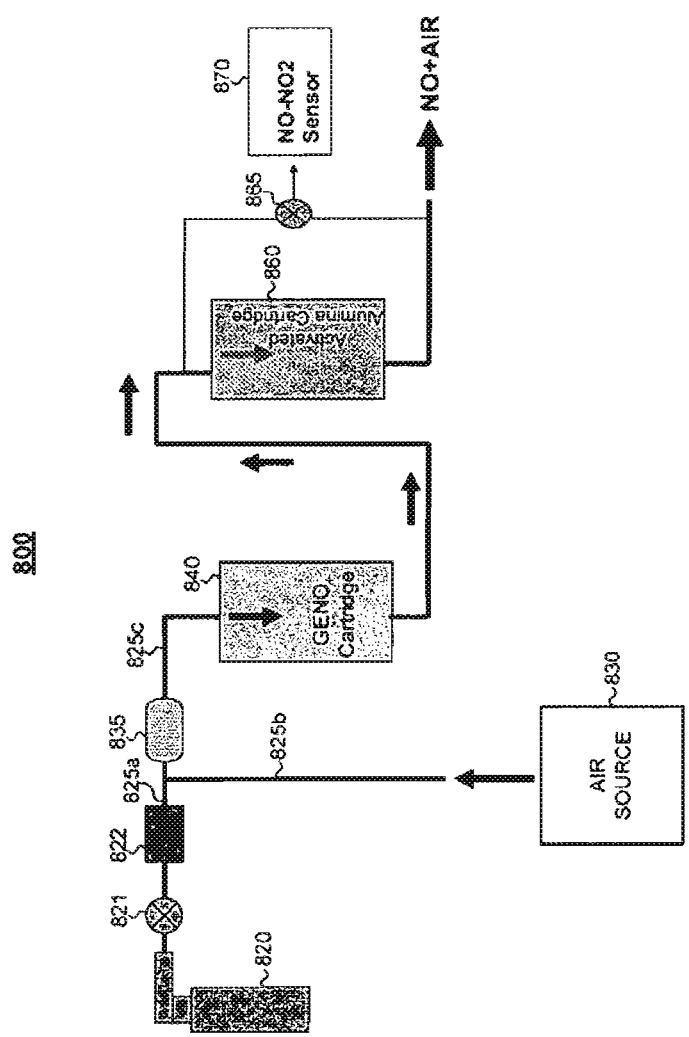

FIG. 8 illustrates a GENO high-concentration $NO_2$ cartridge system 800 for delivering therapeutic gas. In contrast to the systems 600 or 700 of FIGS. 6 and 7, respectively, the system 800 includes a high-concentration $NO_2$ cartridge as the source of the $NO_2$ used to generate the NO. More particularly, the system 800 includes an $NO_2$ cartridge 800, such as a small butane tank or a cartridge conventionally used to deliver $CO_2$. In one example of the system 800, a $NO_2$ cartridge with dimensions of 1 inch by 6 inches and filled with 5% $NO_2$ in $CO_2$ was able to deliver $NO_2$ for 14 days.

A $NO_2$ shut-off valve 821 is adjacent to the cartridge 800 to shut-off delivery of $NO_2$ from the cartridge 800. The system 800 also includes a flow controller 822 to ensure a generally constant flow rate of the flow 825a exiting the flow controller 822. The flow controller 822 is a glass tube with a small hole through which the gas flow 825a passes. In various implementations of the system 800, the flow controller 822 may ensure a constant flow rate of 1 to 10 cc/min.

The gas flow 825a having $NO_2$ exits the flow controller 822 and is mixed with an air flow 825b of approximately 5 L/min that is generated by an air source 830. A gas mixer 835 ensures that the air flows 825a and 825b are fully (or essentially fully) mixed. The resulting air flow 825c with $NO_2$ enters a GENO cartridge 840 that generates NO.

The system 800 also includes an activated alumina cartridge 860 to remove any $NO_2$ before the therapeutic gas including NO is delivered to the patient at the rate of approximately 5 L/min. The system 800 includes a $NO_x$ sample valve 865 and a NO—$NO_2$ sensor 870 operable to detect $NO_2$. In some implementations, the activated alumina cartridge 860 may be replaced with a GENO cartridge.

Figure 9:
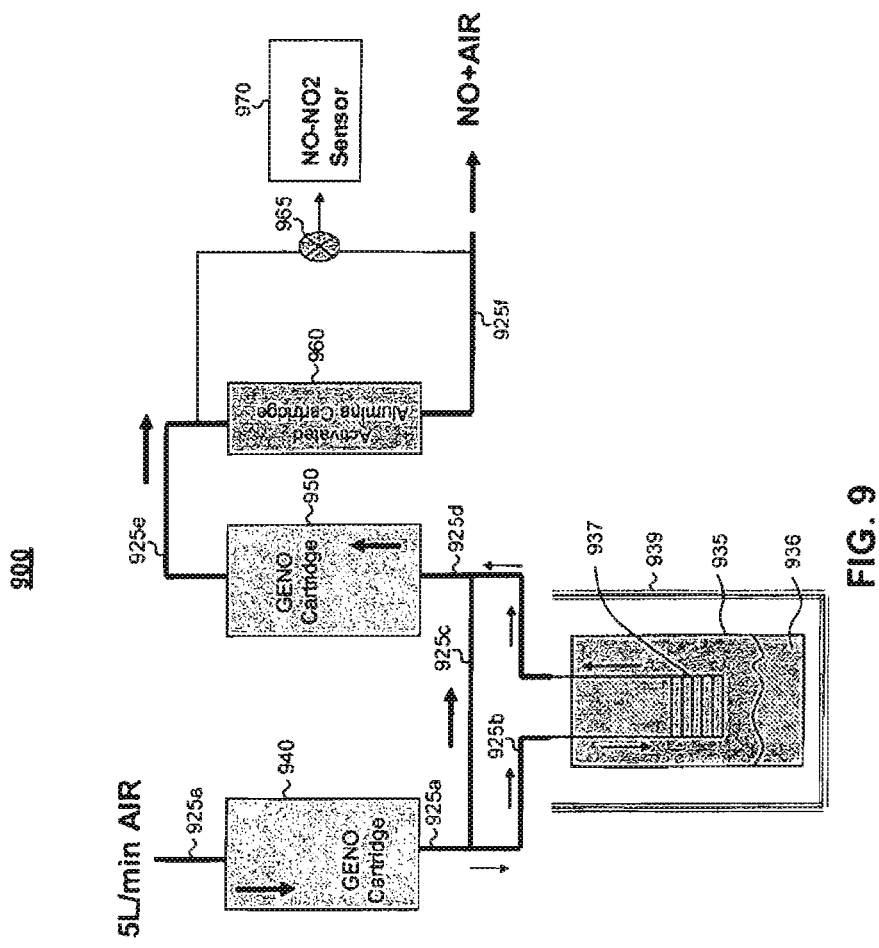

FIG. 9 illustrates a GENO permeation system 900 for delivering therapeutic gas. The system 900 includes an air flow 925a of approximately 5 L/min that flows into a GENO cartridge 940, which acts to humidify the air. After exiting the GENO cartridge 940, the air flow 925a divides such that an air flow 925b passes through a permeation device 935 and an air flow 925c does not. The permeation device 935 includes permeation tubing 937 and about 10 cc of liquid $NO_2$ 936 when the air flow 925a begins. The permeation device 935 may be an implementation of the permeation cell 235 of FIG. 2. The permeation device 935 is in a permeation oven 939 to maintain a constant, or an essentially constant, temperature to ensure the desired concentration of $NO_2$ is diffused into the air flow 925b. The air flow 925b and the air flow 925c mix to form flow 925d before entering the GENO cartridge 950. The GENO cartridge 950 converts the $NO_2$ to NO.

The system 900 also includes an activated alumina cartridge 960 to receive air flow 925e and remove any $NO_2$ before the therapeutic gas including NO is delivered to the patient at the rate of approximately 5 L/min. The air flow 925f that exits the activated alumina cartridge is delivered to a patient for NO inhalation therapy. The system 900 includes a $NO_x$ sample valve 965 and a NO—$NO_2$ sensor 970 operable to detect $NO_2$.

Figure 10:
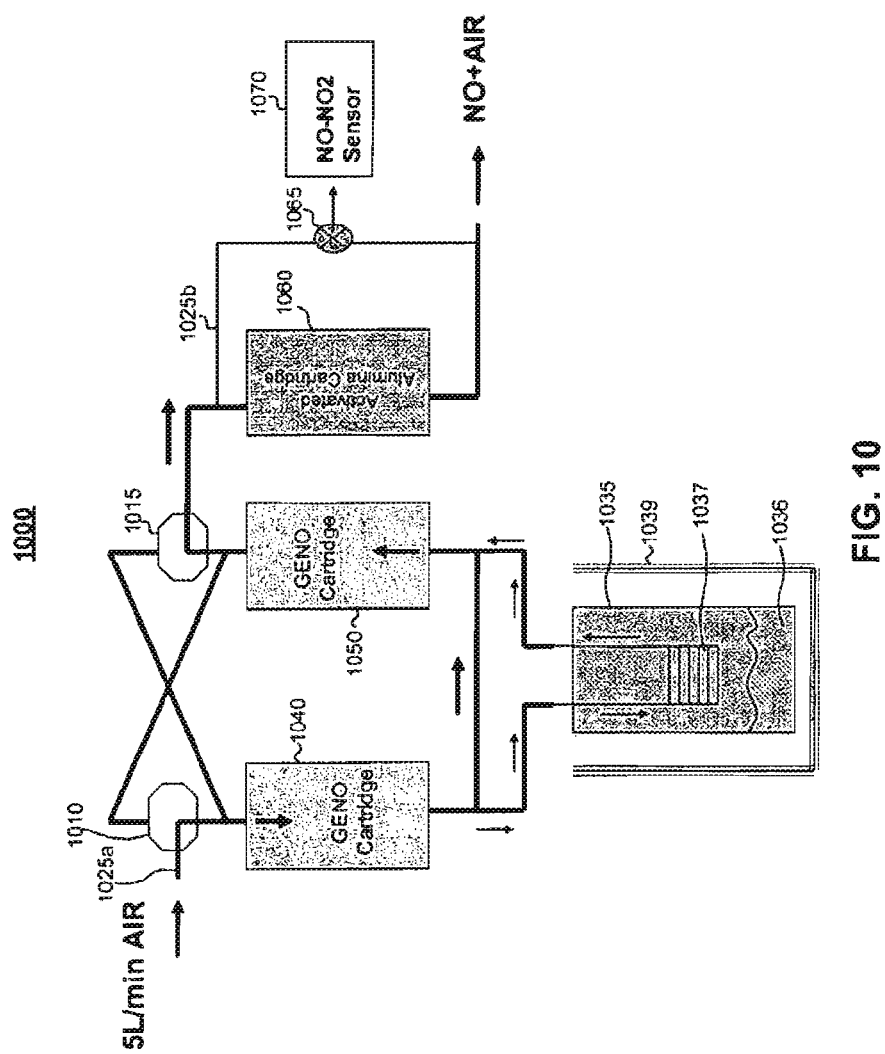

FIG. 10 illustrates a GENO permeation system 1000 for delivering therapeutic gas. In contrast to the system 900 of FIG. 9, the system 1000 includes valves 1010 and 1015 to control which of the GENO cartridges 1040 and 1050 first receives the air flow. The system 1000 uses liquid $NO_2$ in a permeation device 1035 as a source of $NO_2$ to be converted to NO. The system 1000 also includes an activated alumina cartridge 1060 to remove any $NO_2$ before the therapeutic gas including NO is delivered to the patient at the rate of approximately 5 L/min. The system 1000 also includes a NOx sample valve 1065 and a NO—$NO_2$ sensor 1070 operable to detect $NO_2$.

The system 1000 receives an air flow 1025a of approximately 5 L/min into the valve 1010, which, together with the valve 1015, controls which of GENO cartridges 1040 or 1050 the air flow 1025a first passes through. More particularly, by controlling the position of the valves 1010 and 1015, the air flow 1025a can be made to pass through the GENO cartridge 1040, the permeation device 1025, the GENO cartridge 1050, and then the activated alumina cartridge 1060 before being delivered to the patient. By manipulating the position of the valves 1010 and 1015, the air flow 1025a also can be made to pass through the GENO cartridge 1050, the permeation device 1025, the GENO cartridge 1040, and then the activated alumina cartridge 1060 before being delivered to the patient.

For example, when the NO—$NO_2$ sensor 1070 detects the presence of $NO_2$ in the air flow 1025b, this may signal a need to manipulate the valves 1010 and 1015 to cause the order in which the GENO cartridges 1040 and 1050 are used to be switched—that is, for example, when the air flow 1025a flows through the GENO cartridge 1040 before flowing through the GENO cartridge 1050, the values 1010 and 1015 are manipulated to cause the air flow 1025a to flow through GENO cartridge 1050 before flowing through the GENO cartridge 1040.

In some commercial applications, $NO_2$ may be sold at a predetermined concentration of approximately 10 to 100 ppm in oxygen or air.

Figure 11:
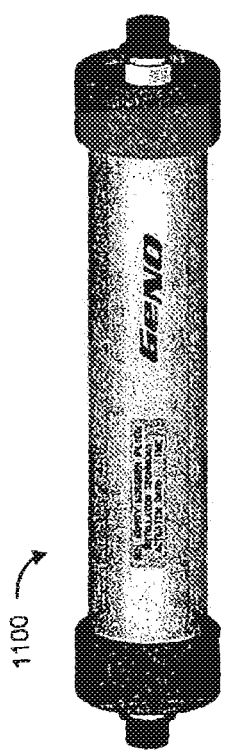
FIG. 11 is a diagram of another cartridge that converts $NO_2$ to NO.

FIG. 11 illustrates a conceptual design of a GENO cartridge 1100 that converts $NO_2$ to NO. The GENO cartridge 1100 may be an implementation of the cartridge 100 of FIG. 1. The GENO cartridge 1100 is approximately 6-inches long with a 1-inch diameter. The GENO cartridge 1100 includes silica gel saturated with an aqueous solution of ascorbic acid and receives an air flow from an air or oxygen gas bottle containing $NO_2$. The air flow through the cartridge 1100 converts $NO_2$ to NO, which exits the cartridge 1100. The GENO cartridge 1100 works effectively at concentrations of $NO_2$ from 5 ppm to 5000 ppm. The conversion of $NO_2$ to NO using the GENO cartridge 1100 does not require a heat source and may be used at ambient air temperature. The conversion of $NO_2$ to NO using the GENO cartridge 1100 occurs substantially independently of the flow rate of the air flow through the GENO cartridge 1100.

Figure 12:
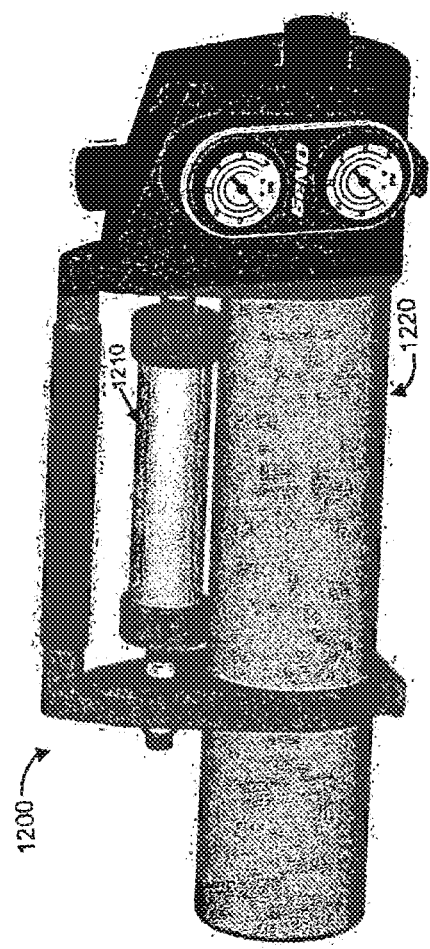
FIGS. 12-14 are diagrams of NO delivery systems using the cartridge of FIG. 11.

FIG. 12 illustrates a therapeutic gas delivery system 1200 that includes a gas bottle 1220 including $NO_2$ and an GENO cartridge 1210, which may be an implementation of GENO cartridge 1100 of FIG. 11, for converting $NO_2$ from the gas bottle 1220 to NO for delivery to a patient for NO inhalation therapy. The system 1200 is designed to be portable. In some implementations, the system 1200 may be designed to operate without the use of electronics or sensors. Depending on the capacity of the gas bottle 1220, the system 1200 generally has capability to deliver therapeutic NO gas for one to sixteen hours.

The system 1200 may be employed to deliver therapeutic NO gas to a patient on an emergency basis. Examples of such contexts include use by paramedics, military medics or field hospitals, firefighters, ambulances, and emergency rooms or a trauma center of a hospital. In another example, a portable therapeutic NO gas delivery apparatus may be used to assist a distressed mountain climber, who may already be breathing oxygen-enriched air. In yet another example, a portable therapeutic NO gas delivery apparatus may be used for a patient whose primary NO source has failed. In some implementations, a portable therapeutic NO gas delivery apparatus may be designed for one-time use.

Figure 13A:
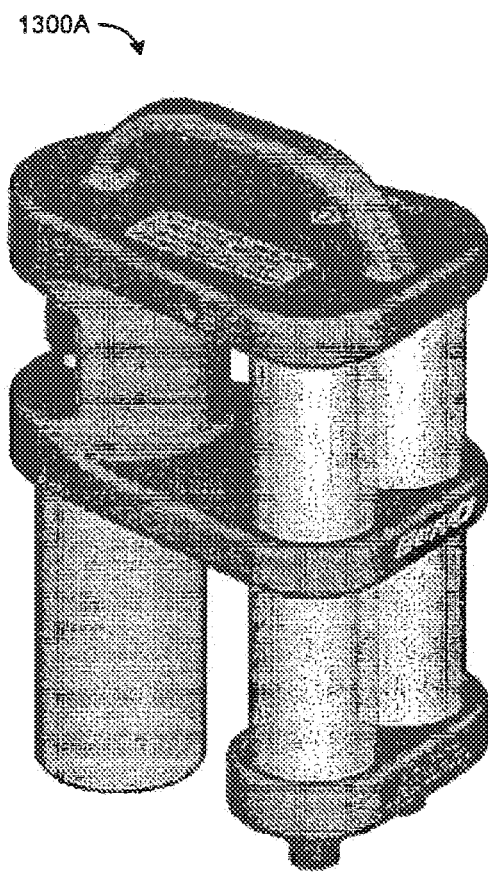
Figure 13B:
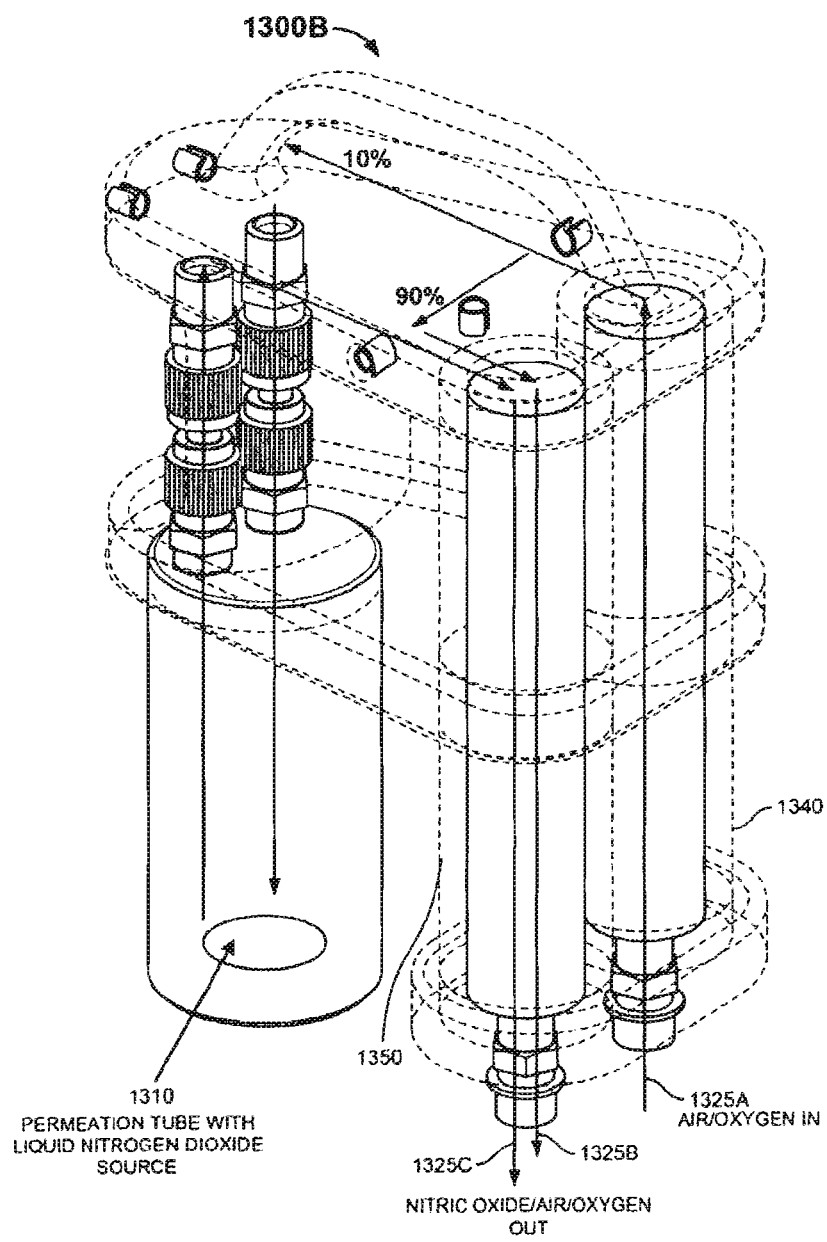

FIG. 13A depicts an exterior view 1300A of a therapeutic gas delivery system with a liquid $NO_2$ source. FIG. 13B illustrates an interior view 1300B of the therapeutic gas delivery system shown in FIG. 13A. The therapeutic gas delivery system includes a permeation tube 1310 with a liquid $NO_2$ source, which, for example, may be an implementation of the permeation device 935 of FIG. 9. The therapeutic gas delivery system also includes GENO cartridges 1340 and 1350. The GENO cartridge 1340 receives an air flow 1325a from an air or oxygen source. After exiting the GENO cartridge 1340, the air flow is divided such that approximately 10% of the air flow flows through the permeation tube 1310 by which gaseous $NO_2$ is diffused into the air flow. The air flow exiting the permeation tube 1310 and the other air flow that did not flow through the permeation tube 1310 flow through the GENO cartridge 1350, which converts the $NO_2$ to NO. The air flows 1325b and 1325c which exit the GENO cartridge 1350 are delivered to the patient for NO inhalation therapy. The permeation tube 1310 and the GENO cartridges 1340 and 1350 may be disposable.

Depending on the capacity of the permeation tube 1310, the therapeutic gas delivery system shown in FIGS. 13A and 13B may have the capability to deliver therapeutic NO gas for one to thirty days.

The therapeutic gas delivery system shown in FIGS. 13A and 13B is able to interface with a ventilator. The therapeutic gas delivery system shown in FIGS. 13A and 13B also may be employed to deliver therapeutic NO gas to a patient using a canella. For example, delivery of the therapeutic NO gas may be provided through a canella at a flow of 2 liters per minute. The use of the therapeutic gas delivery system with a canella may enable NO therapy to occur outside of a hospital setting. One such example is the use of therapeutic gas delivery system for long-term NO therapy that takes place at the patient's home.

FIG. 13C depicts the exterior view 1300A of the therapeutic gas delivery system shown in FIGS. 13A and 13B relative to a soda can 1350. As illustrated, the implementation of the therapeutic gas delivery system shown in FIGS. 13A-13C is a small device relative to conventional NO inhalation therapy systems and is slightly larger than a soda can.

Figure 14:
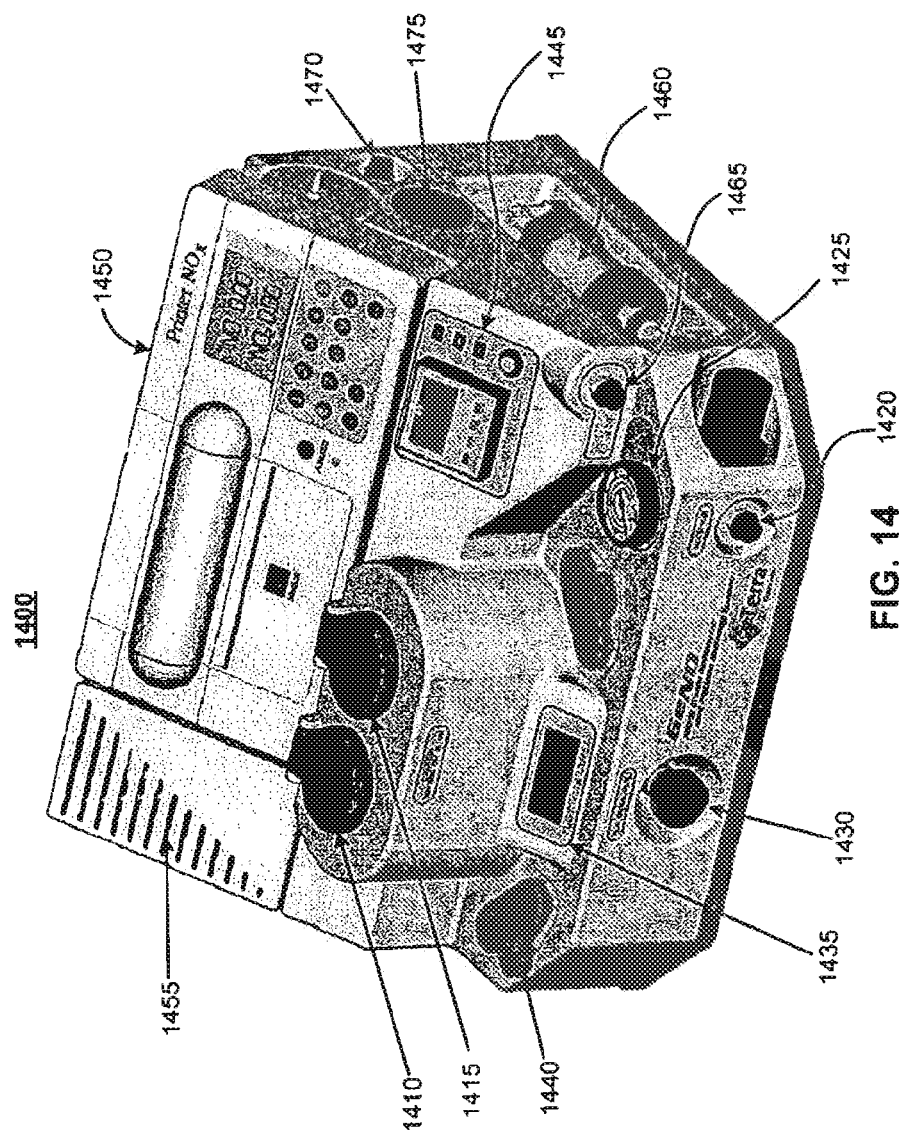

FIG. 14 depicts an exterior view of a therapeutic gas delivery system 1400 that uses GENO cartridges to convert $NO_2$ to NO for use in NO inhalation therapy. The system 1400 includes GENO cartridge ports 1410 and 1415 through which a GENO cartridge may be inserted or accessed. The system 1400 includes an inlet port 1420 through which air or oxygen flows into the system 1400 and an associated gauge 1425. The system 1400 includes a flow value 1430 and display 1435 for controlling the air flow. The system 1400 includes GENO cartridge flow ports 1440.

The system 1400 also includes a temperature controller 1445 and a NOx detector 1450, which is accessible through a NOx detector access 1455. The system 1400 also includes a GENO cartridge 1460 that is used to convert $NO_2$ to NO essentially just before the air flow having NO exits the system 1400 through the outlet 1465. The GENO cartridge 1460 may be referred to as a safety scrubber. The GENO cartridge 1460 may be smaller than the GENO cartridges used elsewhere in the system 1400. The system 1400 also includes a backup input port 1470 and an exhaust fan 1475.

Additional Example Implementations

These additional example implementations use a gas bottle that contains the required dose of NO, stored as $NO_2$, in either oxygen or air or some combination. The gas is converted on release from the gas bottle as follows:

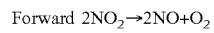

Forward $2NO_2 \rightarrow 2NO+O_2$

This reaction takes place in under a second in the GENO cartridge over Ascorbic acid on a moist silica gel matrix. The pressure of the system should be held to that needed to force the gas through the system. Typically, the force is about 0.001 to 50 psi, for example, between 0.001 and 0.1, or between 0.001 and 0.05 psi. In one embodiment, the pressure of the system can be at 0.005 psi pressure drop above atmospheric pressure at low flow rates of the order of 5 liters per minute. In another embodiment, the pressure drop can be 0.04 psi at gas flows as high as 60 liters per minute. In a further embodiment, the GENO cartridge can work well at about 15 to about 25 psi above atmospheric pressure. As soon as the NO is formed, the reverse reaction occurs, namely:

Reverse $NO+NO+O_2 \rightarrow 2NO_2$

Figure 16:
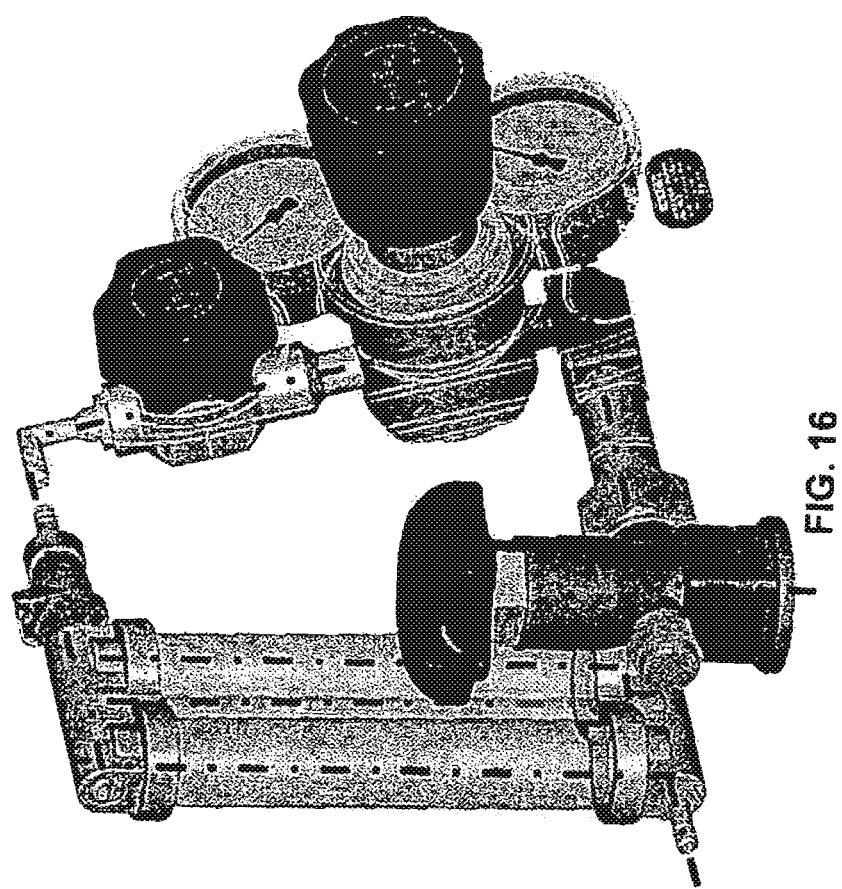
FIG. 16 is a diagram showing placement of the GENO cartridge on the low pressure side of the pressure regulator.

The higher the pressure the faster this reaction occurs; indeed its rate is $3^{rd}$ order in pressure. Converting $NO_2$ to NO on the high pressure side of the regulator may not occur, when the reverse reaction is occurring almost as fast as the forward reaction. To address this challenge, the reverse reaction is minimized by placing the GENO cartridge on the low pressure side of the pressure regulator. This is shown in the FIG. 16 below. Gas exits from the gas bottle, passes thru the regulator and then flows down the first cartridge, up a connecting tube and then down a second cartridge and then out to the user.

Two cartridges are used serially, one after the other. The reason is to offer double redundancy. One cartridge works well, but having a second cartridge provides redundancy. Each cartridge is sized to take the entire contents of the gas bottle with from 40% extra capacity at 100 ppm to 20X extra capacity for 20 ppm. As such, this example implementation uses two identical cartridges, which provides double the back up of the using only one cartridge.

Operation and Safety

Figure 17:
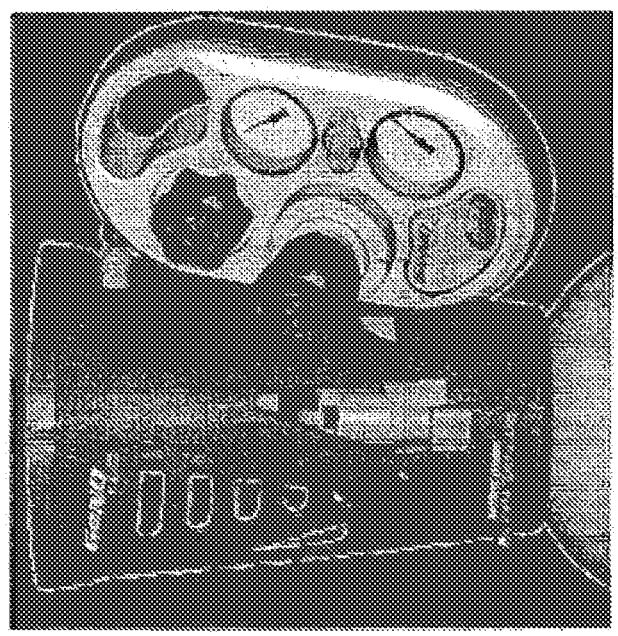
FIG. 17 is a diagram showing a cartridge that is an integral part of a gas bottle cover.

Another approach to increasing the safety of using the system is shipping the cartridges as an integral part of the gas bottle cover. This is shown in FIG. 17 below together with a regulator:

In such an implementation, the user receives the gas bottle and then attaches a special regulator to the gas bottle. Using specially keyed CGA fittings, only a GENO regulator could be used. However, the output of the regulator may be shaped in such a way as to become the inlet port to the GENO cartridge that is attached to the gas bottle cover. Thus, the only way that the user could get gas out of the bottle is to use a regulator with the special CGA fitting, and the only way to get gas out of the regulator would be to connect to the GENO cartridge. In this way, the gas leaving the gas bottle only is able to pass through the GENO cartridges.

Figure 18:
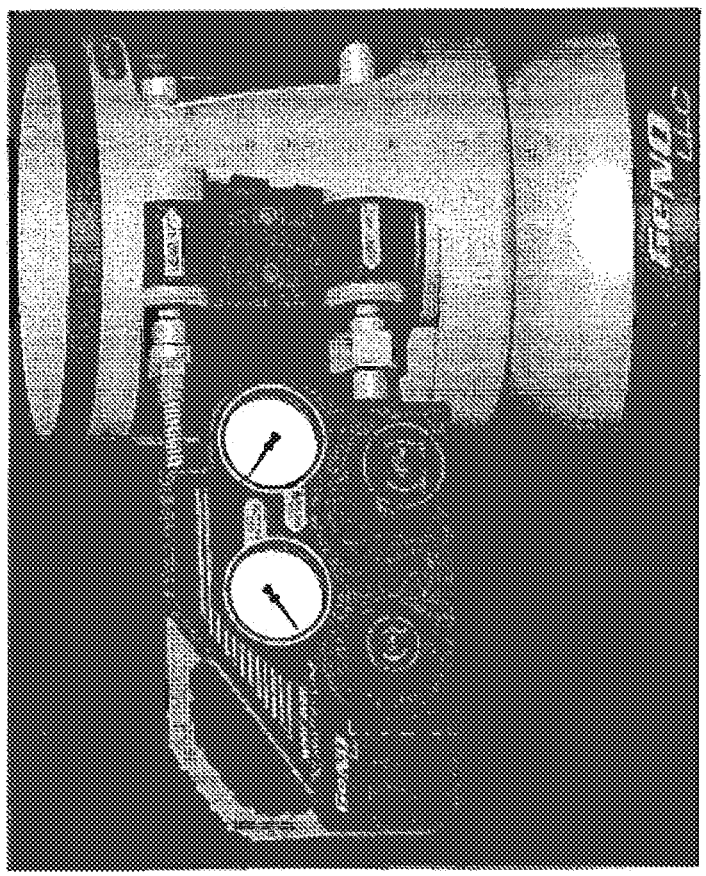
FIG. 18 is a diagram showing a regulator connected to both the outlet of the gas bottle and the inlet of the cartridge.

This is depicted in FIG. 18. The cartridge remains with the gas bottle at all times. For instance, even when the bottle is returned to be refilled, the used cartridge remains on the gas bottle. The gas filler then removes the spent cartridge and replaces the spent cartridge with a new cartridge.

FIG. 18 shows the regulator connected to both the outlet of the gas bottle and the inlet of the cartridge.

For further safety, the output from the cartridge may be keyed as well so that the NO in oxygen gas can only be used with the special adaptor.

In order to vary the concentration of the NO gas, a different gas bottle is used. One way to help identify the concentration of the NO gas in a gas bottle is to have bottles in each concentration have a different color. For example, the bottle with 20 ppm concentration would be blue, whereas the bottle with 100 ppm concentration would be red. Each concentration could have its own specially keyed gas bottles, which also may help reduce or prevent unintentionally using a concentration of the NO gas that is different than the intended concentration to be used. In order to prevent a mix up at the gas bottler, different concentrations may be bottled in different factories—for example, bottles with 100 ppm concentration are bottled at one location, whereas bottles of 20 ppm concentration are bottled at a different location.

Figure 19:
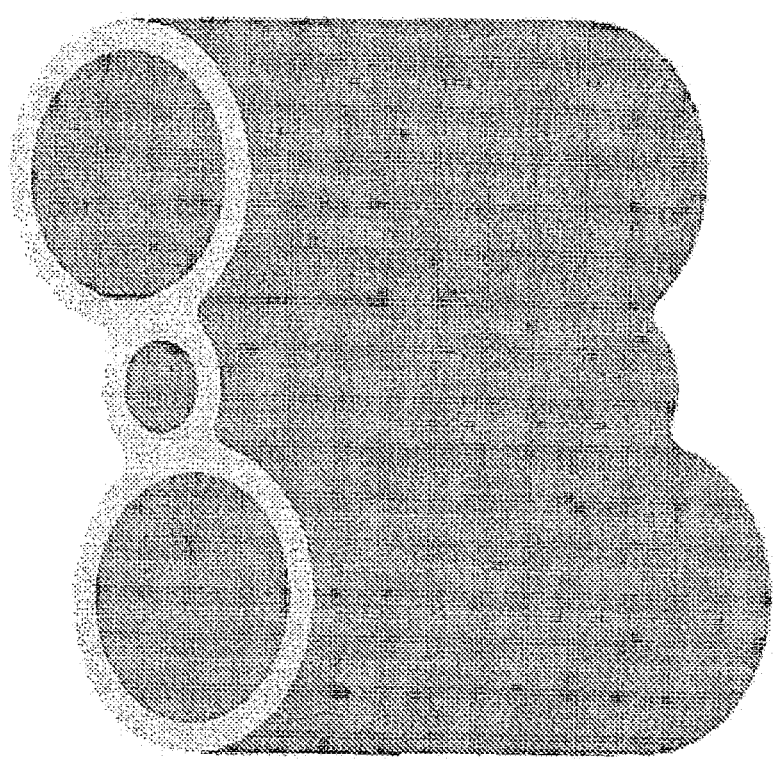
FIGS. 19-21B are diagrams showing aspects of a three-part cartridge design.

In some implementations, the cartridge design may include only 3 parts. The first part is a twin tube with a third passage between the twin tubes, as illustrated in FIG. 19.

Figure 20:
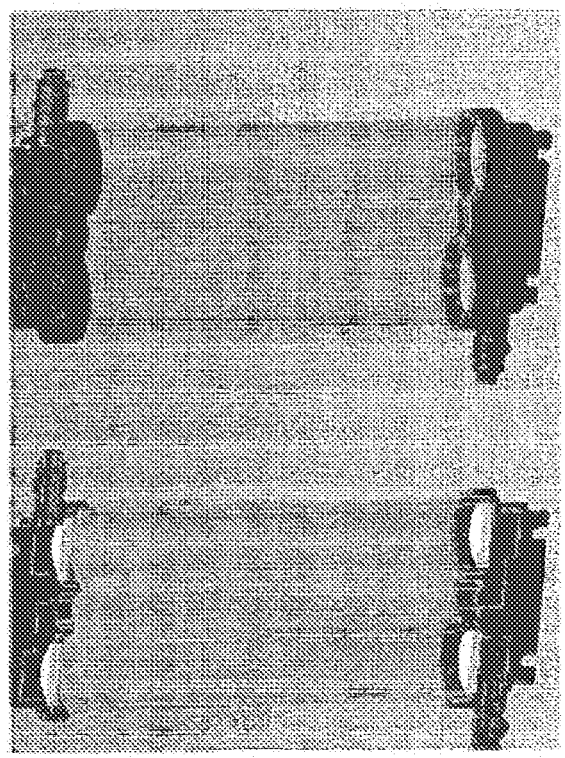

FIG. 20 also depicts twin tubes with a third passage between the twin tubes.

Figure 21A:
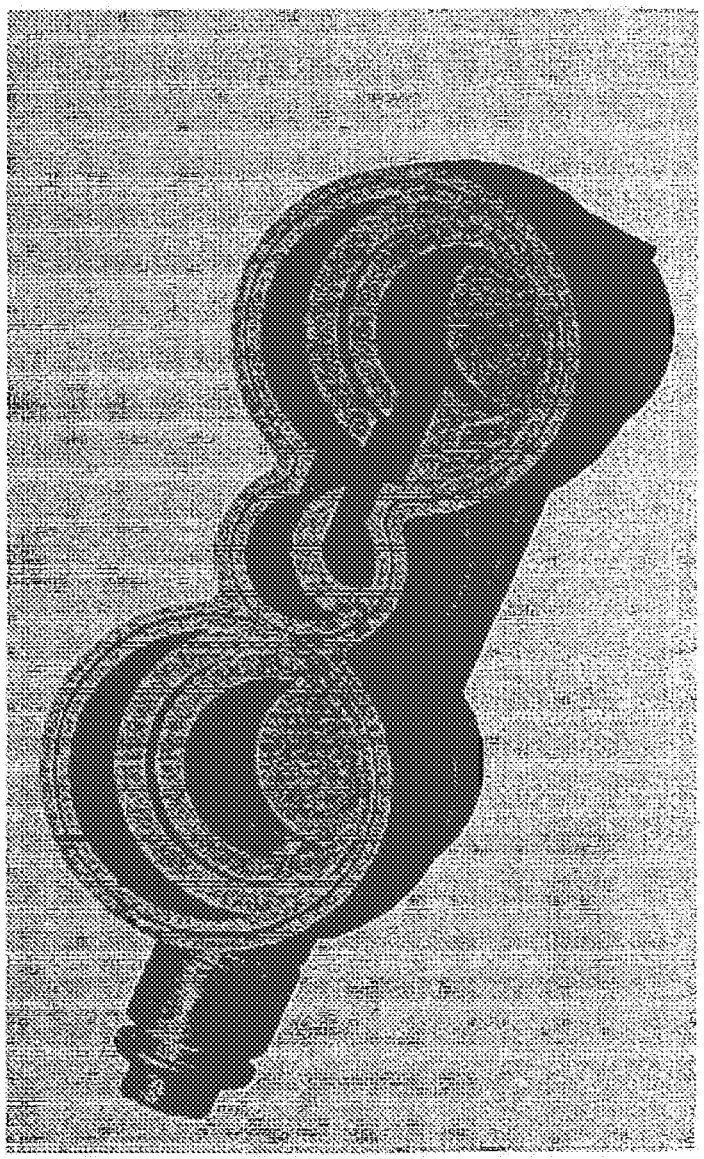
Figure 21B:

The end caps of this three-part cartridge design are shown below in FIGS. 21A and 21B.

The interior of the caps is shaped to take the center tube. Sealing the tubes to the caps to the tube may be accomplished with ultrasonic welding. Sealing the tubes may be accomplished using another technique, such as solvent bonding, O-rings or a clamp seal. A feature of the caps is to mold the male part of the quick disconnect right into the cap; thereby making the entire cartridge a throw away item.

The cartridge may be assembled as follows:
1. A plastic frit, with a pore size such that it holds the powder, is inserted into an end cap.
2. The tube and one end cap are welded together, such that the frit is positioned to act as a filter to prevent powder leaving the cartridge.
3. The tube is filled with the reagent powder. During filling the powder is compressed and vibrated so as to ensure uniform and tight packing and the removal of all voids. Once the tube is filled, the second end cap, with its filter held in place, is placed over the top of the tube and welded in place.
4. If needed, the system is flushed with nitrogen gas to eliminate oxygen from the system.
5. Plastic end caps are placed over the inlet and outlet tubes so as to prevent the entrainment of moisture.

Recuperator Cartridge

Figure 22A:
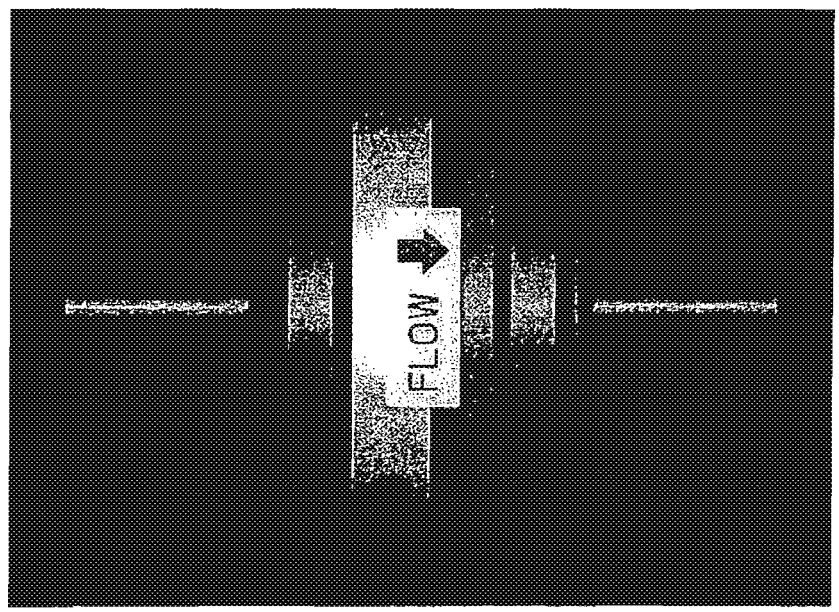
FIGS. 22A-22B are diagrams showing implementations of a recuperator.
Figure 22B:
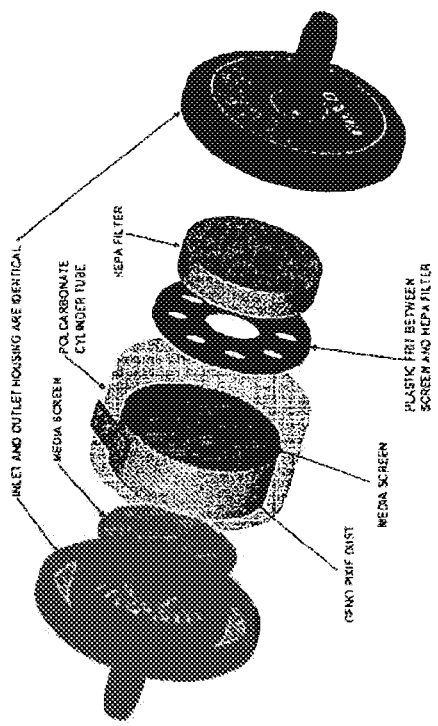

A recuperator cartridge is inserted into the gas plumbing line just prior to inhalation. The purpose of the recuperator is to convert back to NO gas any $NO_2$ gas that may have been formed in the ventilator and during storage in a gas bag or other temporary gas storage device. FIGS. 22A and 22B illustrate other implementations of a recuperator.

Alternatively, the recuperator may be the same size and form as one of the first cartridges. This may further increase the safety of the system in operation. For example, the recuperator would then provide triple redundancy to the system with the recuperator being able to convert the entire contents of the gas bottle from $NO_2$ to NO.

Other Applications

The gas bottle can be used for other applications involving NO. The gas bottle can be used to deliver the bottled gas without the use of electronics. The advantages of the system include simplicity, no mixing, no electronics and no software. To operate, the regulator is connected and the valve opened.

The GENO gas bottle system can also be used with a dilutor. In an example of implementation, the gas is shipped, for example, as 1000 ppm of $NO_2$ in oxygen. In a first stage, the user's equipment dilutes this concentration down to, perhaps, 20 ppm $NO_2$. The second stage inserts the GENO cartridge and converts the gas to NO. A recuperator cartridge helps to reduce the user's concern to about any $NO_2$ that was formed in the gas lines because the $NO_2$ would be converted by to NO by the recuperator. Similarly, the recuperator cartridge could be used with existing system to convert all of the residual $NO_2$ gas being inhaled into the therapeutic form, namely NO. The recuperator also ensures that no NO gas is lost from the system and that the patient is receiving the full prescribed dose.

The fact that GENO can deliver high doses of NO, of the order of 100 to 200 ppm or even higher, without the presence of the toxic form, $NO_2$, may be important. This addresses the difficulty of a delivered dose being limited to around 20 ppm range due to the presence of toxic $NO_2$, which limited the dose that could be achieved. The GENO system eliminates $NO_2$ toxicity problems in the inhaled gas. This may increase, perhaps even greatly increase, the utility of NO gas for treatment of a multitude of diseases, and especially ARDS ("Acute respiratory distress syndrome").

GENO Cartridge $NO_2/O_2$ Gas Bottle Safety

Figure 23:
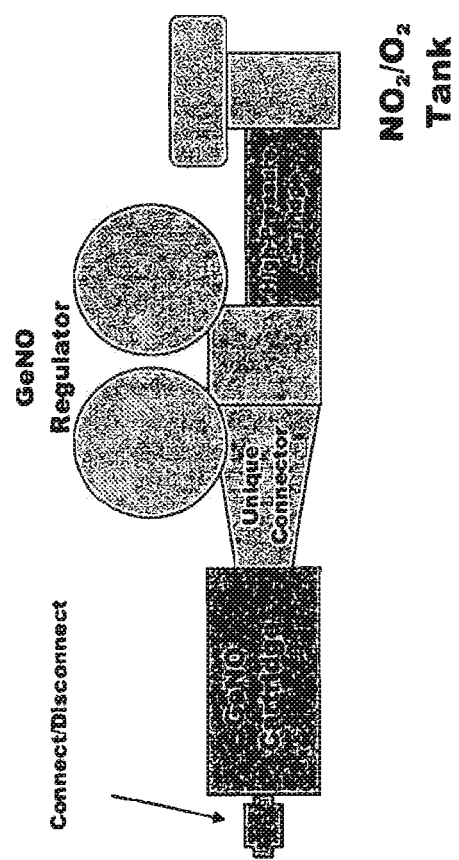
FIG. 23 is a diagram of an NO delivery system using a GeNO cartridge with a specially designed fitting.

In some implementations of the GeNO technology, $NO_2$ is dispensed at about 20 ppm in either oxygen or air and a GeNO cartridge is built onto the high pressure side of the gas bottle. The cartridge has the capacity to convert the entire $NO_2$ (which is toxic) contents of the tank to NO gas, which is non toxic (see FIG. 23). This high-pressure cartridge may be delivered with the tank and designed to be removed only by the tank manufacturer, due to a specially designed fitting. This cartridge also may have a fitting for a regulator with a non-standard connection that permits attachment of the GeNO cartridge (low-pressure) which, in turn, has a connection for regular medical usage. This helps to prevent using the tank without using the low-pressure cartridge, which is a redundant safety cartridge that also has the capacity to convert the entire contents of the $NO_2$ in the tank. This also helps to reduce the possibility that someone may attach a non-GeNO regulator on a gas bottle containing toxic $NO_2$ gas in oxygen or air, as well as reducing the possibility of an accidental release of the tank contents into a room in the absence of a regulator.

Backup System in Case of Primary Device Failure Additionally or alternatively, a second, duplicate apparatus (including tank, regulator and cartridge) is available to permit rapid switching of the patient's input source to another tank.

Permeation Tube

Use of Diffusion Cell

A diffusion cell may help to minimize, or even alleviate, the risks associated with a catastrophic rupture of the permeation tube. A recommended dose of 20 ppm of NO in 5 liters of air per minute amounts to about 0.33 g of $NO_2$ per day. A 10 day supply could have 3 to 4 g of liquid $NO_1/N_2O_4$. If the permeation tube were to rupture suddenly, the contents could escape into the room, creating a serious hazard both for the patent and also for the staff. To help mitigate this safety hazard, the liquid $NO_2$ may be stored in a strong diffusion cell made of stainless steel or a strong plastic. The diffusion cell is connected to the permeation tube by means of a narrow bore hypodermic needle, and acts as the reservoir for the permeation tube. In the event of a catastrophic failure of the permeation tube, the liquid is released slowly over hours to days through the narrow bore needle, thereby avoiding a catastrophic and sudden release of toxic $NO_2$. Furthermore, the diffusion cell can be made strong enough to resist damage from, for example, crushing, dropping onto concrete, or from sharp objects.

Double Redundancy

Figure 24:
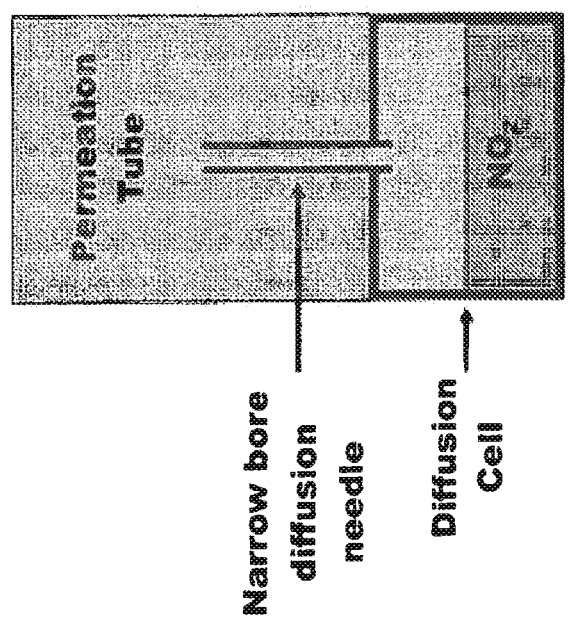
FIG. 24 is a diagram of a diffusion cell connected to a permeation tube.

In some implementations, the diffusion cell is designed to deliver slightly more $NO_2$ than needed by the permeation tube. Thus a cell made of stainless steel with a 4 inch length of hollow tube of 0.002 inch id, would provide enough material to provide slightly more than 20 ppm of $NO_2$ in 5 liters of air per minute at 35 degrees Centigrade. The diffusion rate from the cell should be about 200,000 ng per minute. If used in this way, the diffusion cell acts not only as a safety device, but also as a back up control release mechanism for the permeation tube. Even in the event of a catastrophic and sudden failure of the permeation tube, the diffusion cell continues to supply the appropriate dose. As such, the diffusion tube is used as a storage device for a permeation tube, and the permeation tube and the diffusion cell work in tandem to provide double redundancy for safety. (See FIG. 24).

Temperature Effects on Permeation and Diffusion

The permeation rate and/or diffusion rate of $NO_2$ from the permeation tube and/or the diffusion cell is dependent upon the temperature. In the case of NO2, the rate increases by a factor of about 1.9 for every 10° C. increase in temperature. In the typical uses of permeation tubes and diffusion cells, this rate increase is controlled by controlling the temperature. For the GENO application, it may be desirable to supply the gas in the temperature range of approximately 15 to 35 degrees C., without controlling the temperature. This may be accomplished, for example, using the following concepts and techniques.

Permeation Tube.

Figure 25:
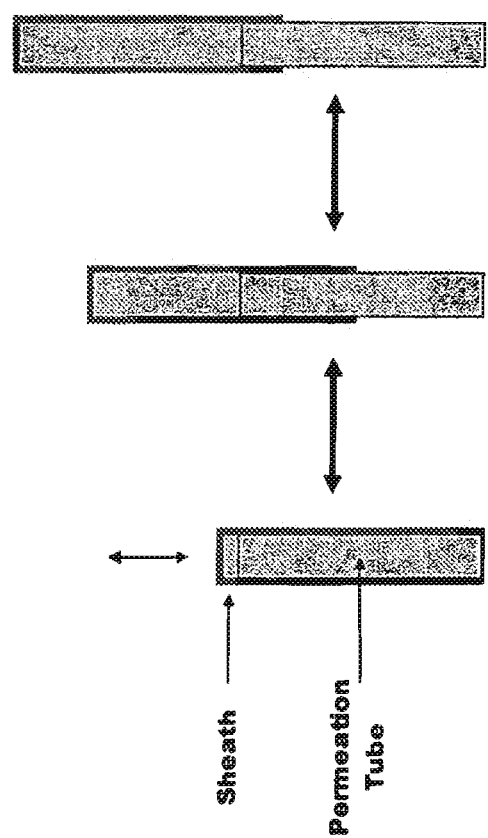
FIG. 25 is a diagram of a permeation tube with a movable, sliding, non-permeable sheath.

In a permeation tube, the amount of material that can permeate is directly proportional to the length of the tube. Thus, a longer tube can deliver more $NO_2$ than a shorter one. With this in mind, using a movable, sliding, non-permeable sheath, one is be able to adjust the amount of permeation tube that is exposed to regulate the delivery of $NO_2$ for a given temperature (see FIG. 25). The length of the tube is scaled to provide the appropriate dose at the lowest design temperature. For this example, the tube is designed to deliver approximately 200,000 ng/min at 15 degrees Centigrade. A sleeve is provided which slides over the tube and covers about ¾ of the length of the tube. Thus, at 15 degrees Centigrade, the entire tube is exposed. If the temperature were 25 degrees Centigrade, the rate of diffusion from the tube is doubled, and this would be compensated for by covering ½ of the active length of the tube. At 35 degrees Centigrade, only ¼ of the tube would be needed to maintain the same permeation rate of approximately 200,000 ng per minute.

It is contemplated that in a hospital environment where the temperatures are well controlled, the system would be fitted with a manual slide calibrated in degrees Centigrade, and the sheath would be set at the temperature of the room. A thermometer could also be attached to the device for added accuracy. A $NO_2$ cartridge is contemplated that includes a dial that is adjusted for a given temperature in the patient's room that slides the sheath on the permeation tube to the appropriate position, providing the appropriate $NO_2$ concentration for conversion to NO.

Diffusion Cell.

The rate of release from the diffusion cell is generally proportional to the length of the narrow bore diffusion needle. In one approach, holes are present in the side of the needle at the ¼, ½, ¾ marks. The three holes are offset so as to be in the front, the side and the rear of the needle. An outer sheath with the appropriate slots is fitted around the needle. By turning the outer sheath, the hole at the ¼ mark is uncovered at 15 degrees Centigrade, whereas all the side holes are covered at 35 degrees Centigrade.

In a second approach, the diffusion cell is fitted with four equal narrow bore needles, with each needle being attached to a short permeation tube. Using this approach, the number of tubes is changed, depending upon the temperature.

In these example implementations, the number of tubes mentioned and the number of holes are examples only and are not meant to limit the application of the contemplated techniques.

NO Weaning-Off Dosage (5 ppm)

Figure 26:
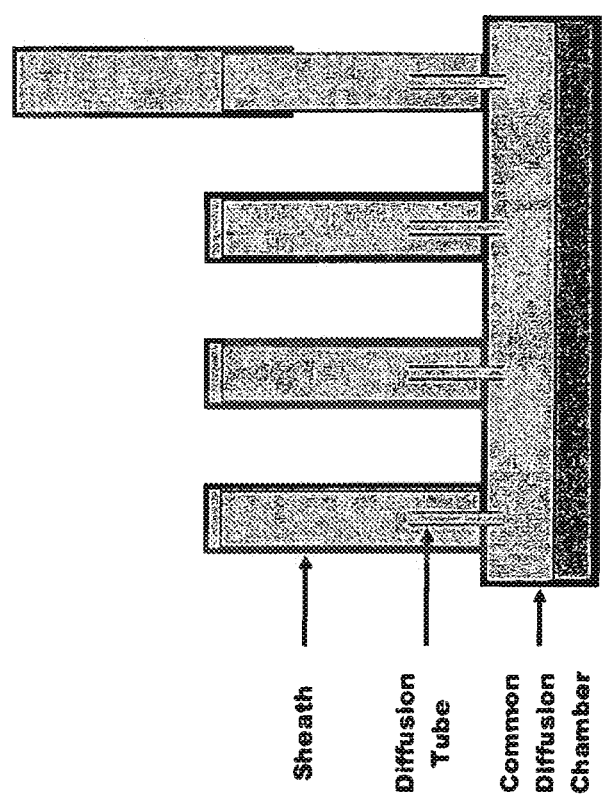
FIG. 26 is a diagram of a common diffusion chamber connected to diffusion tubes, and permeation tubes.

As with temperature control, the dosage can also be controlled by using the sheath, or varying the number of tubes. A dial on one tube may be attenuated to permit the release of a quarter of the amount of $NO_2$ (assuming full calibration is for a 20 ppm dosage of NO) required to provide a 5 ppm weaning-off dosage of NO to the patient. Additionally, if four tubes are used in the $NO_2$ cartridge to provide 20 ppm NO dosage, the dial can cover three of the permeation tubes, leaving the fourth tube to provide the 5 ppm dosage while permitting temperature adjustments (see FIG. 26). There are various permutations of this, based upon the discussion provided above.

Rapid Equilibration

One of the challenges in using permeation tubes for medical dosage is that they can take a long time to come to equilibrium. Because the permeation tube is always permeating and cannot be switched off, the tube may deliver an initial over dose if the tube was sealed, without air flow, into its permeation chamber. It has been observed to take four hours or more for the tube to reach equilibrium and deliver the correct dose. By covering the active area of the tube with an impermeable sheath, such as a heavy walled Teflon or stainless steel or glass (see FIG. 25), the permeation of the $NO_2$ may be blocked during shipping and storage, and substantially shortens, perhaps greatly shortens, the time needed to achieve equilibrium. The sheath can be removed just prior to use and generally 1 hour or less is needed to equilibrate to the calibrated dosage. By covering the active area of the tube with an impermeable sheath, equilibrium may be reached relatively more quickly while helping to prevent an initial over dose that may otherwise occur if the tube was sealed, without air flow, into its permeation chamber while not being used for inhalation therapy.

Transport/Rupture Safety

Reinforcement of the diffusion chamber that contains the liquid $NO_2$, combined with the use of the diffusion cells also helps to prevent the escape of toxic $NO_2$ in the event of a permeation tube rupture. Additionally, having the sheaths fully lowered, sealing the permeation tubes from the $NO_2$ cartridge chamber during transportation and storage, and when not in use, helps to provide protection for the tubes.

The use of the sheaths also protects the permeation tube when it is used without the diffusion cell.

Transport/Temperature Safety

In some implementations, special heat sensitive ink can be put on the $NO_2$ cartridge to indicate exposure to overly high temperatures. The ink notifies users not to use the cartridge, since the heat might cause the permeation tubes to over-pressurize and make them more sensitive to rupture. Air-tight seals on the cartridge should help prevent pressure differentials between the inside and outside of the permeation tubes.

Example 1

A cartridge six-inches in length with a diameter of 1.5-inches was used as the NO generation cartridge. Approximately 90 grams 35-70 sized mesh silica gel was soaked in a 25% ascorbic acid solution and air-dried at room temperature for two hours before being placed in the cartridge. A $NO_2$ permeation tube was used as the source gas for $NO_2$. Air from an air pump at a rate of 150 cc/min was flowed into the permeation tube and mixed, after it exited the cartridge, with 3 L/min of ambient air (which also was from the air pump). The permeation tube was placed in an oven with a temperature set at 32 degrees Celsius to provide a steady stream of 20 ppm $NO_2$ for the cartridge. The cartridge lasted for 269 hours before ceasing to convert 100% of NO2 to NO, achieving breakthrough.

Example 2

Two cartridges were each filled using 35-70 sized mesh silica gel and approximately 40 grams of silica gel. The silica gel was prepared by being soaked with a 25% solution of ascorbic acid until complete saturation, and then dried in an oven for one hour at 240 degrees Fahrenheit. The ascorbic acid solution was prepared by mixing 25 grams of ascorbic acid in 100 ml of de-ionized water.

A 1000 ppm $NO_2$ tank was used to flow $NO_2$ through the two GENO cartridges at a rate of 150 cc/min. The two cartridges were placed in series. Ambient air from an air tank was mixed in after the $NO_2$ had passed through the first cartridge and been converted to NO. The air containing NO was then passed through the through the second cartridge in series. The air was passed through the cartridges at a rate of 3 L/min to create a total mixture of 40 ppm NO in air and free of any back reaction of $NO_2$.

The two cartridges converted 100% of the $NO_2$ for 104 hours. At the end of 104 hours, the experiment was stopped because the $NO_2$ tank was empty. The two cartridges had not yet reached breakthrough after 104 hours.

Results may be improved by drying the silica gel with a gas, such as nitrogen gas, to remove dripping water/ascorbic acid solution from the silica gel.

Example 3

A plastic PVC cartridge six-inches in length and having a diameter of 1.5-inches was used as the NO generator cartridge. The inside of the cartridge was filled with an ascorbic acid-silica mixture. To create the ascorbic acid silica mixture, approximately 108 grams of 35-70 sized mesh was used. The silica gel was soaked in 25% ascorbic acid solution and then baked in an oven for one hour at 240 degrees Fahrenheit. The ascorbic acid solution was prepared by dissolving 25 grams of ascorbic acid in 100 ml of de-ionized water.

A 1000 ppm $NO_2$ tank was attached to one end of the cartridge so that 1000 ppm of $NO_2$ flowed through the cartridge at a rate of 150 cc/min. The gas output of the cartridge was then mixed with air using an air pump that flowed at a rate of 3 L/min to create a total mixture of 40 ppm NO in air. This cartridge lasted for a total of 122 hours before achieving breakthrough.

A NOx detector detected a slight concentration of $NO_2$, varying from 0.15 ppm to 0.25 ppm. The concentration of $NO_2$ remained steady until breakthrough, making it likely that the detected $NO_2$ concentration was not a failure in the 100% efficiency of the cartridge but rather was $NO_2$ that was recreated in tubing after the cartridge. A second, smaller cartridge could be placed before the detector to eliminate the small $NO_2$ back reaction.

Example 4

A cartridge was prepared by using 35-70 sized mesh silica gel soaked in 25% ascorbic acid solution and air dried for approximately one hour. A permeation tube was the source for the $NO_2$ and a KinTek oven was used to raise the level of $NO_2$ required to 40 ppm. To achieve this concentration, the oven was set at 45 degrees Celsius. Air was delivered to the permeation tube using an air pump at the rate of 200 cc/min. Dilution air was also provided by the air pump at the rate of 3 L/min. To add humidity to the supply of $NO_2$, two jars filled with water were attached to the 200 cc/min air before the air entered the permeation tube. This helped to ensure that the air entering the $NO_2$ source would be moisture rich and therefore that the $NO_2$ entering the cartridge would also be moisture rich. Approximately every five days, the water in the first jar receded to below the end of the tubing and needed to be replenished so that the water level was above the bottom of the tube end. The second jar remained untouched for the entire length of the experiment. The cartridge lasted for 409 hours before ceasing to convert 100% of NO2 to NO, achieving breakthrough.

Example 5

A cartridge six-inches long and having a diameter of 1.5-inches was prepared by using 108 grams of 35-70 sized mesh silica gel. The silica gel was soaked in a 25% solution of ascorbic acid solution and dried at room temperature (approximately 70 degrees Fahrenheit) for approximately two hours. The air-dried silica gel was placed inside the cartridge.

A flow of 40 ppm $NO_2$ was sent through the silica-ascorbic acid cartridge at a rate of 3.2 L/min. The cartridge lasted for 299 hours before ceasing to convert 100% of $NO_2$ to NO, achieving breakthrough. The cartridge filled with air-dried silica gel lasted longer than a comparable cartridge filled with oven-dried silica gel. This demonstrates oxidation losses due to heating the ascorbic acid in the presence of air.

Example 6

Approximately 40 grams of 35-70 sized mesh silica gel was soaked in a 33% ascorbic acid solution and the dried in an oven at 240 degrees Fahrenheit before being placed in the cartridge. Ambient air at a flow rate of 3 L/min though an air pump was mixed with 1000 ppm of $NO_2$ from a tank at a flow rate of 200 cc/min, which created a total flow rate of 3.2 L/min and a total $NO_2$/air mixture of 60 ppm $NO_2$. The cartridge lasted for 25 hours before losing its 100% conversion ability. This demonstrates that using less silica gel/ascorbic acid in the cartridge results in a cartridge that does not last as long.

The use of NO generation cartridge in which $NO_2$ is quantitatively converted to NO is not limited to therapeutic gas delivery and may be applicable to many fields. For example, the NO generation cartridge may be included in an air pollution monitor. More particularly, the NO generation cartridge can also be used to replace high temperature catalytic convertors that are widely used today in air pollution instrumentation measurement of the airborne concentration of $NO_2$ gas. The current catalytic convertors expend significant electricity, and replacement of a catalytic convertor with a device that uses a NO generation cartridge may simplify the air pollution instruments, and enable lower cost, reduced weight, portable air pollution monitoring instruments.

Figure 15:
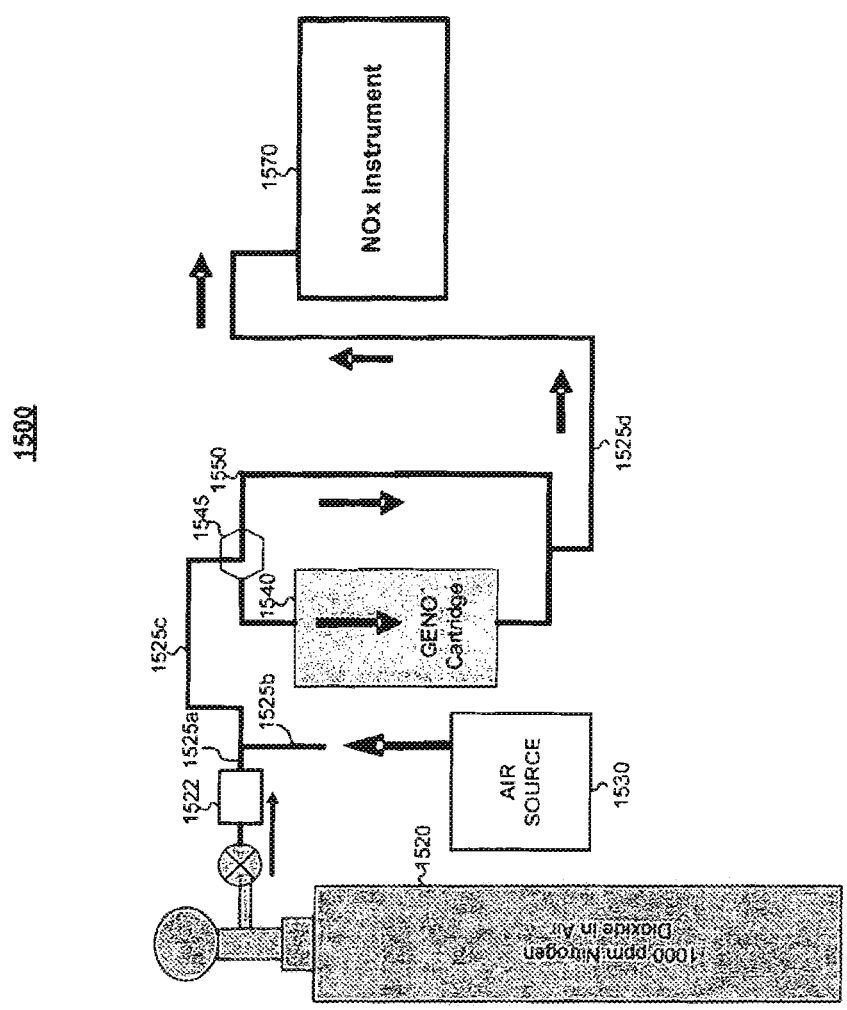
FIG. 15 is a block diagram of a NOx instrument calibration system using the cartridge of FIG. 1.

In another exemplary use, a NO generation cartridge may be used in a NOx calibration system. FIG. 15 illustrates an example of a NOx calibration system 1500 that includes a tank 1520 having 1000 ppm $NO_2$ in air and a flow controller 1522. In the example of FIG. 15, the tank 1520 is an implementation of tank 722 in FIG. 7.

An air flow 1525*a* of $NO_2$ in air exits the flow controller 1522 and is mixed with an air flow 1525*b* of 5 L/min that is generated by an air source 1530, such as an air pump. The resulting air flow 1525*c* enters the switching valve 1545. The switching valve 1545 controls whether the GENO cartridge 1540 receives the air flow 1525*c* for conversion of the $NO_2$ in the air flow 1525*c* to NO. As shown, the switching valve 1545 is set such that the air flow 1525*c*, rather than being provided to the GENO cartridge 1540, is provided to tubing 1550.

The system 1500 includes a NOx instrument 1570 that is to be calibrated to detect NO and $NO_2$. The NOx instrument 1570 receives the air flow 1525*d* that includes NO when the air flow 1525*c* is directed by switching valve 1545 to the GENO cartridge 1540. In contrast, the air flow 1525*d* includes $NO_2$ when the air flow 1525*c* is directed by switching valve 1545 to the tubing 1550.

The NOx calibration system 1500 requires a single pressurized tank that includes $NO_2$ to calibrate the NOx instrument 1570 for both NO and $NO_2$. To do so, for example, the NOx instrument 1570 first may be calibrated for NO by using the switching valve 1545 to direct the air flow 1525*c* through the GENO cartridge 1540 (which converts the $NO_2$ in the air flow 1525*c* to NO). The NOx instrument 1570 then may be calibrated for $NO_2$ by using the switching valve 1545 to direct the air flow 1525*c* through the tubing 1550, which results in the air flow 1525*d* including $NO_2$. In addition, NOx calibration system 1500 does not require the use of heat to convert $NO_2$ to NO, for example, to ensure that there is no inadvertent exposure to $NO_2$ during calibration.

Other implementations are within the scope of the following claims.

What is claimed is:

1. A system, comprising:
   a pressure regulator configured to diffuse gaseous nitrogen dioxide into an air flow, the pressure regulator including a diffusion cell configured to be connected to a source of the gaseous nitrogen dioxide; and
   a receptacle fluidically coupled to the pressure regulator, the receptacle including a surface-active material coated with an aqueous solution of an antioxidant configured to convert the gaseous nitrogen dioxide to nitric oxide.

2. A system, comprising:
   a pressure regulator configured to diffuse gaseous nitrogen dioxide into an air flow;
   a receptacle fluidically coupled to the pressure regulator, the receptacle including a surface-active material coated with an aqueous solution of an antioxidant configured to convert the gaseous nitrogen dioxide to nitric oxide; and
   a cartridge disposed downstream of the receptacle and configured to remove nitrogen dioxide from the air flow.

3. The system of claim 2, wherein the cartridge includes activated alumina.

4. The system of claim 2, further comprising:
   a sample valve coupled to the cartridge and configured to provide samples of the air flow; and
   a sensor fluidically coupled to the sample valve, the sensor configured to detect nitrogen dioxide present in the samples of the air flow.

5. A system, comprising:
   a diffusion cell configured to diffuse gaseous nitrogen dioxide into an airflow;
   a receptacle fluidically coupled to the diffusion cell, the receptacle including a surface-active material wetted with an aqueous solution of an antioxidant configured to convert the gaseous nitrogen dioxide to nitric oxide; and
   a cartridge downstream of the receptacle, the cartridge configured to remove nitrogen dioxide from the air flow.

6. The system of claim 5, wherein the antioxidant includes ascorbic acid.

7. The system of claim 5, wherein the cartridge includes activated alumina.

8. The system of claim 5, further comprising:
   a sample valve coupled to the cartridge and configured to provide samples of the air flow; and
   a sensor fluidically coupled to the sample valve, the sensor configured to detect nitrogen dioxide present in the samples of the air flow.

* * * * *